(12) United States Patent
Deng et al.

(10) Patent No.: US 9,040,567 B2
(45) Date of Patent: May 26, 2015

(54) BAX AGONIST, COMPOSITIONS, AND METHODS RELATED THERETO

(75) Inventors: Xingming Deng, Lilburn, GA (US); Jia Zhou, League City, TX (US); Chunyong Ding, Shanghai (CN)

(73) Assignees: Emory University, Atlanta, GA (US); Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 14/239,177

(22) PCT Filed: Aug. 17, 2012

(86) PCT No.: PCT/US2012/051420
§ 371 (c)(1),
(2), (4) Date: Feb. 21, 2014

(87) PCT Pub. No.: WO2013/028543
PCT Pub. Date: Feb. 28, 2013

(65) Prior Publication Data
US 2014/0178374 A1    Jun. 26, 2014

Related U.S. Application Data

(60) Provisional application No. 61/525,249, filed on Aug. 19, 2011, provisional application No. 61/648,887, filed on May 18, 2012.

(51) Int. Cl.
| | | |
|---|---|---|
| A61K 31/05 | (2006.01) |
| C07D 213/73 | (2006.01) |
| C07D 213/74 | (2006.01) |
| C07C 271/16 | (2006.01) |
| C07C 205/11 | (2006.01) |
| C07C 205/25 | (2006.01) |
| C07C 205/35 | (2006.01) |
| C07C 309/65 | (2006.01) |
| C07C 311/21 | (2006.01) |
| C07C 211/52 | (2006.01) |
| C07C 215/88 | (2006.01) |
| C07C 217/20 | (2006.01) |
| C07C 217/26 | (2006.01) |
| C07C 217/94 | (2006.01) |
| C07C 233/18 | (2006.01) |
| C07C 233/25 | (2006.01) |
| C07C 233/80 | (2006.01) |
| C07D 209/10 | (2006.01) |
| C07D 295/088 | (2006.01) |
| C07D 211/46 | (2006.01) |
| C07D 295/185 | (2006.01) |
| C07D 295/26 | (2006.01) |
| C07D 213/61 | (2006.01) |
| C07D 213/64 | (2006.01) |
| A61K 31/085 | (2006.01) |
| A61K 31/138 | (2006.01) |
| A61K 31/404 | (2006.01) |

(Continued)

(52) U.S. Cl.
CPC .............. *A61K 31/05* (2013.01); *C07D 213/73* (2013.01); *C07D 213/74* (2013.01); *C07C 271/16* (2013.01); *C07C 205/11* (2013.01); *C07C 205/25* (2013.01); *C07C 205/35* (2013.01); *C07C 309/65* (2013.01); *C07C 311/21* (2013.01); *C07C 211/52* (2013.01); *C07C 215/88* (2013.01); *C07C 217/20* (2013.01); *C07C 217/26* (2013.01); *C07C 217/94* (2013.01); *C07C 233/18* (2013.01); *C07C 233/25* (2013.01); *C07C 233/80* (2013.01); *C07D 209/10* (2013.01); *C07D 295/088* (2013.01); *C07D 211/46* (2013.01); *C07D 295/185* (2013.01); *C07D 295/26* (2013.01); *C07D 213/61* (2013.01); *C07D 213/64* (2013.01); *C07C 2101/02* (2013.01); *C07C 2103/18* (2013.01); *A61K 31/085* (2013.01); *A61K 31/138* (2013.01); *A61K 31/404* (2013.01); *A61K 31/44* (2013.01); *A61K 31/4412* (2013.01); *A61K 31/4465* (2013.01); *A61K 31/495* (2013.01); *A61K 31/5375* (2013.01); *A61K 45/06* (2013.01); *C07C 217/60* (2013.01); *C07D 209/12* (2013.01); *C07D 213/643* (2013.01)

(58) Field of Classification Search
USPC ........ 514/351, 471.6, 728; 544/154; 546/285; 564/315
IPC ............................... A61K 45/06; C07D 209/12
See application file for complete search history.

(56) References Cited

U.S. PATENT DOCUMENTS

| | | | |
|---|---|---|---|
| 3,331,687 A | 7/1967 | Kosche |
| 5,344,841 A | 9/1994 | Jiang |

(Continued)

FOREIGN PATENT DOCUMENTS

| | | |
|---|---|---|
| BE | 623849 | 2/1963 |
| WO | 2006019955 | 2/2006 |

OTHER PUBLICATIONS

Yan et al. CAS: 134: 4720, 2000.*

(Continued)

*Primary Examiner* — Rei-Tsang Shiao
(74) *Attorney, Agent, or Firm* — Emory Patent Group

(57) ABSTRACT

The disclosure relates to BAX activators and therapeutic uses relates thereto. In certain embodiments, the disclosure relates to methods of treating or preventing cancer, such as lung cancer, comprising administering a therapeutically effective amount of a pharmaceutical composition comprising a compound disclosed herein or pharmaceutically acceptable salt to a subject in need thereof.

8 Claims, 8 Drawing Sheets

(51) Int. Cl.
- A61K 31/44 (2006.01)
- A61K 31/4412 (2006.01)
- A61K 31/4465 (2006.01)
- A61K 31/495 (2006.01)
- A61K 31/5375 (2006.01)
- A61K 45/06 (2006.01)
- C07C 217/60 (2006.01)
- C07D 209/12 (2006.01)
- C07D 213/643 (2006.01)

(56) References Cited

U.S. PATENT DOCUMENTS

| | | | |
|---|---|---|---|
| 5,436,243 | A | 7/1995 | Sachs |
| 5,733,880 | A | 3/1998 | Mincher |
| 6,465,522 | B1 | 10/2002 | Potter |
| 7,799,782 | B2 * | 9/2010 | Munson et al. ............ 514/234.5 |
| 2008/0096848 | A1 | 4/2008 | Kemnitzer | |

OTHER PUBLICATIONS

Kawaguchi et al. CAS: 124: 160300, 1995.*
Annunziata et al. Synthesis and structural assignment of 2,4'-disubstituted benzylidenefluorenes and 4'-substituted benzylidene-1-azafluorenes Magn. Reson. Chem. 36 (1998).
Epstein et al. On the Association between Photodynamic and Enzyme-inducing Activities in Polycyclic Compounds, Cancer Research 31, 1087-1094, 1971.
Yan & Sun, KF-AI2O3 Induced the Condensation of 2-Nitrofluorene and Para-Substituted Acetophenones With Aromatic Aldehydes, Synthetic Communications, 30(20), 3809-3814 (2000).
Zheng et al., Ultrasonicated Condensation of Indene and 2-Nitrofluorene with Aromatic Aldehydes Catalyzed by bis-(pMethoxyphenyl)telluroxide (BMPTO), Synthetic Communications, 27(10), 1751-1755 (1997).
Xin & Deng, Nicotine Inactivation of the Proapoptotic Function of Bax through Phosphorylation, J. Biol. Chem. 2005, 280:10781-10789.
Pepper et al., Bcl-2/Bax ratios in chronic lymphocytic leukaemia and their correlation with in vitro apoptosis and clinical resistance, British Journal of Cancer (1997) 76(7), 935-938.
Xin et al. Small-molecule Bax agonists for cancer therapy, Nature Communications, 2014, 5:4935.
Gardai et al. Phosphorylation of Bax Ser184 by Akt regulates its activity and apoptosis in neutrophils. J. Biol. Chem. 279, 21085-21095 (2004).
Takano et al. A diaminoantraquinone inhibitor of angiogenesis, J Pharmacol Exp Ther, 1994, 271(2):1027-33.
Zhong et al. Studies on the reaction of organotelluronium salts, Chinese Chemical Letters (1991), 2(1), 51-4.
Teodorescu et al. Determination of current-voltage characteristics of 2,4'-bis(trimethylammoniumacetamido)•benzalfluorene dichloride, Studii si Cercetari de Fizica (1979), 31(8), 797-801.
Radulescu & Horst, Quaternary ammonium salts of acetamidobenzalfluorene, Revue Roumaine de Chimie (1970), 15(7), 1127-36.
Dobrescu, Derivatives of 2-nitro- and 2,7-dinitrofluorene. Studii Cercetari Stiint., 3. 1956, Ser. I, No. 3-4, p. 45-65.
Candea et al. Several derivatives of fluorene. Bull. Etudes et Recherches Tech. (Bucharest), 1949, vol. 1, p. 83-90.
Candea et al. Fluorene nitro derivatives. II. Colored reaction given by some derivatives of 2-nitrofluorene. Bull. Soc. Chim. France, 1936, vol. 3, p. 1761-1767.
Loevenich et al. Condensation of 2-nitrofluorene with aromatic aldehydes. J. 1-5,7,8 Prakt. Chem. (Leipzig), 1927, vol. 116, p. 325-330.

* cited by examiner

Scheme 1. Synthesis of Compounds A1-3.

Scheme 2. Synthesis of Compounds B1-12.

Scheme 3. Synthesis of Compounds C1-6.

Scheme 4. Synthesis of Compounds D1-4.

| Compounds | A549-P IC50 | A549-IRR IC50 |
|---|---|---|
| CYD-2-11: | 3.89 uM | 3.93 uM |
| CYD-3-77: | 8.23 uM | 38.24 uM |
| CYD-4-44: | 9.03 uM | 22.84 uM |
| CYD-4-36: | 9.12 uM | 40.81 uM |
| CYD-4-61: | 0.034 uM | 0.026 uM |

FIGURE 7

BAX AGONIST, COMPOSITIONS, AND METHODS RELATED THERETO

CROSS REFERENCE TO RELATED APPLICATIONS

This application claims priority to U.S. Provisional Application No. 61/525,249 filed on 19 Aug. 2011 and U.S. Provisional Application No. 61/648,887 filed 18 May 2012, both hereby incorporated by reference in their entirety.

ACKNOWLEDGEMENT

This invention was made with government support under Grant R01CA160489 awarded by the National Institutes of Health. The government has certain rights in the invention.

BACKGROUND

BAX, a member of the BCL-2 (B-cell lymphoma-2) family, is a nuclear-encoded protein that is able to pierce the mitochondrial outer membrane to mediate cell death by apoptosis. BAX adopts a globular α-helical structure and converts into pore-forming protein by changing conformation and assembling into oligomeric complexes in the mitochondrial outer membrane. Proteins from the mitochondrial intermembrane space then empty into the cytosol to activate proteases that degrade the cell.

Cancer cells are able to evade apoptosis by the dysregulation of pro- and anti-apoptotic Bcl-2 family proteins. The expression of BAX appears to play an important role in suppressing cancer development and decreased BAX levels contribute to chemoresistance in a number of cancers, including, but not limited to, lung cancer, chronic lymphocytic leukemia (CLL), and prostate cancer, and. See Xin & Deng, J Biol Chem., (2005), 280, 10781-10789; Pepper et al., Br J Cancer, (1997) 76: 935-8. Because BAX is extensively expressed in both small cell lung cancer and non-small cell lung cancer cells, BAX agonists could be particularly useful for treating lung cancer. Thus, there is a need to identify compounds that activate BAX.

SUMMARY

This disclosure relates to BAX activators and therapeutic uses relates thereto. In certain embodiments, the disclosure relates to methods of treating or preventing cancer, such as lung cancer, comprising administering a therapeutically effective amount of a pharmaceutical composition comprising a compound disclosed herein or pharmaceutically acceptable salt to a subject in need thereof. In certain embodiments, the disclosure relates to compounds or derivatives, prodrugs, or esters of compounds disclosed herein optionally substituted with one or more substituents.

In certain embodiments, the disclosure relates to compounds of Formula I,

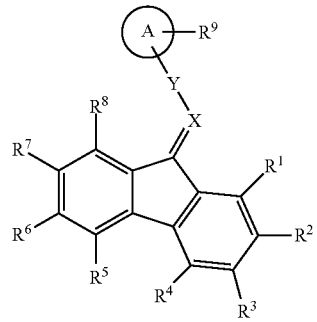

Formula I or salt thereof wherein,
----- is a double or single bond;
A ring is a carbocyclyl, aryl, or heterocyclyl;
X is CH or N;
Y is $(CH_2)_n$ or a direct bond to the A ring, wherein n is 1 or 2;
$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;
$R^2$ is nitro or amino wherein $R^2$ is optionally substituted with one or more, the same or different, $R^{10}$;
$R^9$ is hydroxy, alkoxy, or amino, wherein $R^9$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^3$, $R^4$, $R^5$, $R^6$, $R^7$, and $R^8$ are hydrogen and ----- is a double bond.

In certain embodiments, A ring is phenyl ortho-, meta- or para-substituted with $R^9$ wherein $R^9$ is hydroxy, alkoxy, alkylamino, or substituted with hydroxy, (alkyl)$_2$amino, alkylsulfamoyl, dialkylsulfamoyl, or a heterocyclyl such as pyrrolidinyl, morpholinyl, piperazinyl, wherein heterocyclyl may be substituted with one or more $R^{12}$, Y is a direct bond to the A ring, X is CH, $R^2$ is nitro, amino, amide, urea, or sulfonamide wherein $R^2$ is substituted with one or more $R^{11}$.

In certain embodiments, the A ring is aryl or heterocyclyl such as pyridinyl ortho- or meta- or para-substituted with $R^9$ and $R^2$ is nitro.

In certain embodiments, $R^2$ is amide, urea, or sulfonamide substituted with alkyl or aryl, and $R^9$ is hydroxyl.

In certain embodiments, ----- is a double bond, X is N, and $R^9$ is alkoxy.

In certain embodiments, ----- is a single bond, Y is a direct bond to the A ring.

In certain embodiments, ----- is a double bond, Y is $(CH_2)_n$ wherein n is 1.

In certain embodiments, the disclosure relates to pharmaceutical compositions comprising compounds disclosed herein such as those of Formula I, IA, IB, or II or pharmaceutically acceptable salts and a pharmaceutically acceptable excipient. In certain embodiments the pharmaceutical compositions further comprising a second therapeutic agent.

In certain embodiments, the disclosure relates to methods of treating or preventing cancer comprising administering a pharmaceutical composition comprising compounds disclosed herein such as those of Formula I, IA, IB, or II to a subject diagnosed with, exhibiting symptoms of, or at risk of cancer. In certain embodiments, the cancer is selected from the group consisting of leukemia, melanoma, cervical, ovarian, colon, breast, gastric, lung, skin, ovarian, pancreatic, prostate, head, neck, and renal cancer. In certain embodiments, the pharmaceutical composition is administered in combination with a second chemotherapeutic agent such as, but not limited to, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine, paclitaxel, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In certain embodiments, the disclosure relates to therapeutic methods disclosed herein wherein the pharmaceutical compositions are administered before, after or during radiotherapy.

In certain embodiments, the disclosure relates to uses of compounds disclosed herein in the production of a medicament for the treatment or prevention of cancer.

In certain embodiments, the disclosure relates to methods of preparing compounds disclosed herein comprising mixing starting materials and reagents disclosed herein under conditions that the compounds are formed.

In certain embodiments, the disclosure relates to methods of inhibiting phosphorylation of BAX at Ser184.

In some embodiments, the disclosure relates to methods of testing compounds for the ability to inhibit BAX phosphorylation comprising mixing a compound and a BAX protein and assaying for phosphorylation at Ser184 by comparing the ability of nicotine to phosphorylate Ser184 after exposing BAX to a test compound.

BRIEF DESCRIPTION OF THE FIGURES

FIG. 7 shows activity data for embodiments in A549 lung cancer parental cells (A549-P) and radiation resistant cells (A549-IRR).

DETAILED DESCRIPTION

Figure 1:
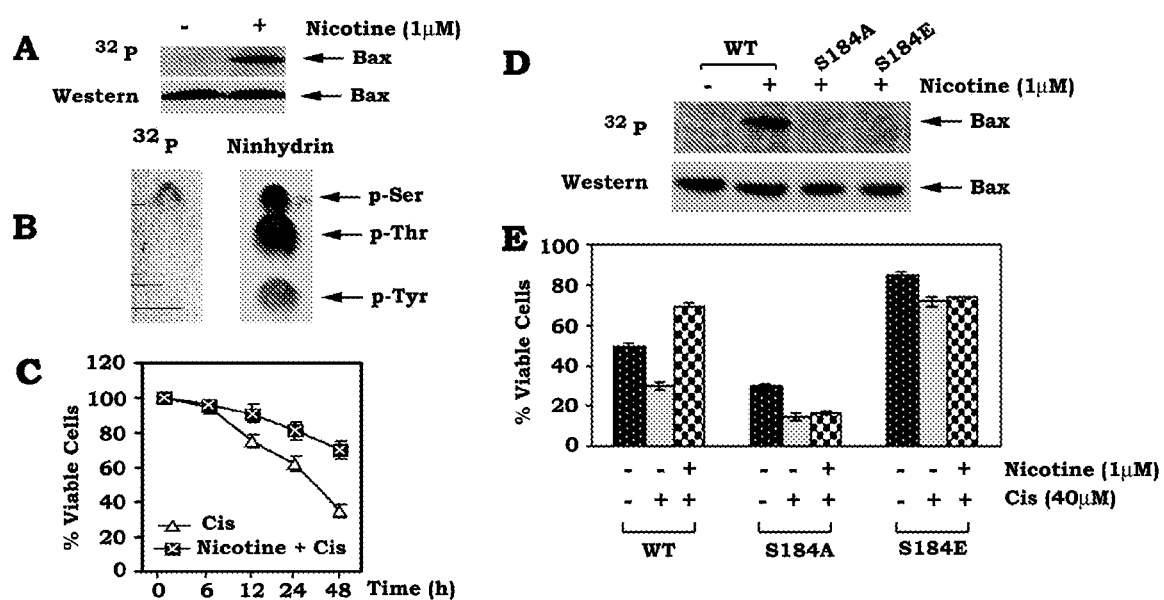
FIG. 1 shows data suggesting phosphorylation of BAX with nicotine at Ser 184 inactivates the proapoptotic function of BAX. (A) A549 cells expressing endogenous BAX were metabolically labeled with $^{32}$P-orthophosphoric acid and treated with nicotine for 60 min. BAX was immunoprecipitated by using an agarose-conjugated BAX antibody. Phosphorylation of BAX was determined by autoradiography. (B) Phosphoamino acid analysis was performed using the phosphorylated BAX induced by nicotine. (C) A549 cells were treated with cisplatin (40 μM) in the absence or presence of nicotine (1 μM) for various times as indicated. Cell viability was analyzed for Annexin-V and PI binding by flow cytometry. (D) The pcDNA3 plasmids bearing GFP-WT, GFP-S184A or GFP-184E were transfected into H157 cells. Cells were metabolically labeled with $^{32}$P-orthophosphoric acid and treated with nicotine for 60 min. Phosphorylated GFP-tagged BAX was analyzed by autoradiography. (E) The pcDNA3 plasmids bearing GFP-WT, GFP-S184A or GFP-184E were transfected into H157 cells. After 48 h, cells were treated with cisplatin (Cis) in the absence or presence of nicotine for 24 h. Cell viability was analyzed as in (C).

BAX is a Bcl-2 family protein. Human BAX isoform alpha has an amino acid sequence of MDGSGEQPRG GGPTSSE-QIM KTGALLLQGF IQDRAGRMGG EAPELALDPV PQDASTKKLS ECLKRIGDEL DSNMELQRMI AAVDTDSPRE VFFRVAADMF SDGNFNWGRV VALFY-FASKL VLKALCTKVP ELIRTIMGWT LDFLRERLLG WIQDQGGWDG LLSYFGTPTW QTVTIFVAGV LTASLTIWKK MG (SEQ ID NO:1). A pocket is located in the hydrophobic C-terminal tail of BAX, which regulates the subcellular location and its ability to insert into mitochondrial membranes. Phosphorylation or dephosphorylation of BAX at Ser184 negatively or positively regulates the proapoptotic activity of BAX. Ser184 residue was chosen as a docking site for screening of small molecules that activate BAX using the computerized DOCK suite of programs and a database of 300,000 small molecules from the National Cancer Institute (NCI) filtered to follow the Lipinski rules. It has been discovered that certain compounds activate BAX. Thus, in certain embodiments, the disclosure relates to compounds disclosed herein, salts, substituted forms, and derivatives. In certain embodiments, the disclosure contemplates pharmaceutical compositions containing these compounds for use in the treatment or prevent of BAX related diseases or conditions such as cancer.

Compounds

In certain embodiments, the disclosure contemplates compounds as provided for in Formula I below,

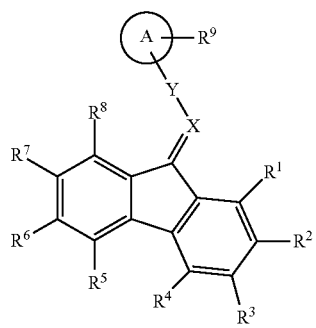

Formula I or salts thereof wherein,

----- is a double or single bond;

A ring is a carbocyclyl, aryl, or heterocyclyl;

X is CH or N;

Y is $(CH_2)_n$ or a direct bond to the A ring, wherein n is 1 or 2;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino wherein $R^2$ is optionally substituted with one or more, the same or different, $R^{10}$;

$R^9$ is hydroxy, alkoxy, or amino, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$, $R^3$, $R^4$, $R^5$, $R^6$, $R^7$, and $R^8$ are hydrogen.

In certain embodiments, ----- is a double bond.

In certain embodiments, A ring is phenyl ortho-, meta- or para-substituted with $R^9$ wherein $R^9$ is hydroxy, alkoxy, alkylamino, or substituted with hydroxy, (alkyl)$_2$amino, alkylsulfamoyl, dialkylsulfamoyl, or a heterocyclyl such as pyrrolidinyl, morpholinyl, piperazinyl, wherein heterocyclyl may be substituted with one or more $R^{12}$.

In certain embodiments, Y is a direct bond to the A ring.

In certain embodiments, X is CH.

In certain embodiments, $R^2$ is nitro, amino, amide, urea, or sulfonamide wherein $R^2$ is substituted with one or more $R^{11}$.

In certain embodiments, the A ring is an aryl or heterocyclyl such as pyridinyl ortho- or meta- or para-substituted with $R^9$.

In certain embodiments, $R^2$ is nitro.

In certain embodiments, X is N.

In certain embodiments, $R^9$ is alkoxy.

In certain embodiments, Y is a direct bond to the A ring.

In certain embodiments, Y is $(CH_2)_n$ wherein n is 1.

In certain embodiments, the compounds of Formula I have Formula IA,

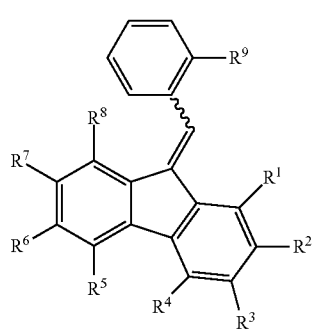

Formula IA or salts thereof wherein, $R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino optionally substituted with one or more, the same or different, $R^{10}$;

$R^9$ is hydroxy, alkoxy, or amino, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds of Formula I have Formula IB,

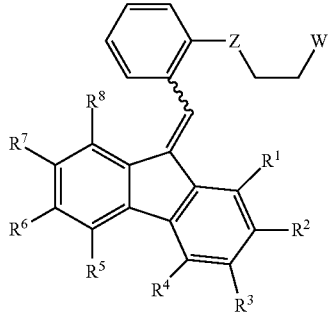

Formula IB or salts thereof wherein,

Z is O, S, $CH_2$, or NH;

W is hydroxy, amino, alkylamino, dialkylamino, aryl, or heterocyclyl wherein W is optionally substituted with one or more $R^{11}$;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds of Formula I have Formula IC,

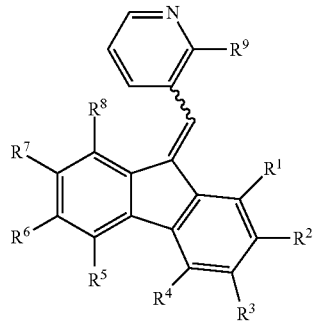

Formula IC or salts thereof wherein, $R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino optionally substituted with one or more, the same or different, $R^{10}$;

$R^9$ is hydroxy, alkoxy, or amino, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds of Formula I have Formula ID,

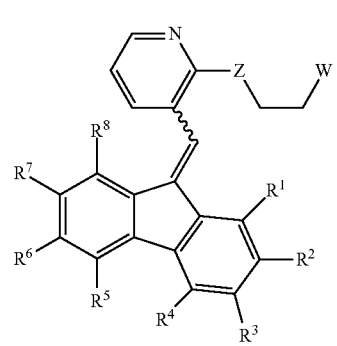

Formula ID or salts thereof wherein,

Z is O, S, $CH_2$, or NH;

W is hydroxy, amino, alkylamino, dialkylamino, aryl, or heterocyclyl wherein W is optionally substituted with one or more $R^{11}$;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of Formula II,

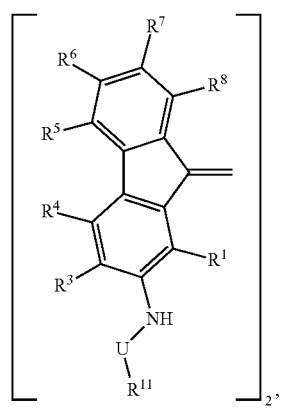

Formula II or salts thereof wherein,

U is —C(═O)— or —SO$_2$—;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compounds as provided for in Formula Ic below are provided,

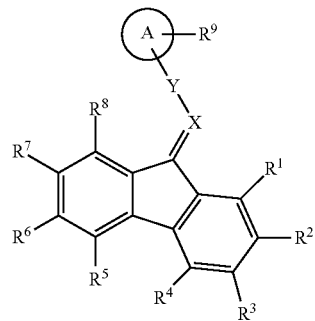

Formula Ic or salts thereof wherein,

----- is a double or single bond;

A ring is a carbocyclyl, aryl, or heterocyclyl;

X is CH or N;

Y is $(CH_2)_n$ or a direct bond to the A ring, wherein n is 1 or 2;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different, $R^{10}$;

$R^2$ is nitro or amino wherein $R^2$ is optionally substituted with one or more, the same or different, $R^{10}$;

$R^9$ is hydroxy, alkoxy, amino, halo, a heterocycle (such as piperazine), or an amide, urea or sulfonamide, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^9$ is halogen. In certain other embodiments, $R^9$ is a heterocycle.

Combination Therapies

The cancer treatments disclosed herein can be applied as a sole therapy or can involve, conventional surgery or radiotherapy or chemotherapy. Such chemotherapy can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies, and approaches using the immunomodulatory drugs thalidomide and lenalidomide [Revlimid®].

Formulations

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet (2006) 21(3):173-85, entitled "Human carboxylesterase isozymes: catalytic properties and rational drug design."

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or can not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

Terms

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH3).

"Alkanoyl" refers to an alkyl as defined above attached through a carbonyl bride (i.e., —(C═O)alkyl).

"Alkylsulfonyl" refers to an alkyl as defined above attached through a sulfonyl bridge (i.e., —S(═O)$_2$alkyl) such as mesyl and the like, and "Arylsulfonyl" refers to an aryl attached through a sulfonyl bridge (i.e., —S(═O)2aryl).

"Alkylsulfinyl" refers to an alkyl as defined above attached through a sulfinyl bridge (i.e. —S(═O)alkyl).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)2Ra, —OS(═O)2Ra and —S(═O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It can also be identified by a change in relevant biomarker or gene expression profile, such as PSA for prostate cancer, HER2 for breast cancer, or others.

EXPERIMENTAL

Phosphorylation at Ser 184 Results in Inactivation of the Proapoptotic Function of BAX The growth factor GM-CSF-induced BAX phosphorylation results in a markedly decreased proapoptotic activity of BAX. Gardai et al., J Biol Chem, 2004, 279, 21085-21095. To test whether BAX phosphorylation occurs in human lung cancer cells, A549 cells were metabolically labeled and treated with nicotine (1 µM) for 60 min. Results indicate that nicotine potently stimulates serine phosphorylation of BAX (FIGS. 1A&B). Intriguingly, nicotine significantly prolongs survival of A549 cells following cisplatin treatment (FIG. 1C), which may occur in a mechanism likely, at least in part, through BAX phosphorylation. To test whether nicotine induces BAX phosphorylation at ser184, WT, S184A or S184E cDNA in the pcDNA3 mammalian expression vector was transfected into H157 cells. Results indicate that nicotine induces phosphorylation of WT but not S184A or S184E mutant BAX (FIG. 1D), suggesting that nicotine stimulates BAX phosphorylation exclusively at ser184 site. Importantly, expression of the nonphosphorylatable S184A results in more apoptotic cell death as compared to WT. Nicotine can prolong survival of cells expressing WT BAX but not the S184A BAX mutant (FIG. 1E). In contrast, the phosphmimetic S184E BAX exhibits no apoptotic activity. Nicotine has no additional survival effect in cells expressing the S184E BAX mutant (FIG. 1E). These findings reveal that either nicotine-induced ser184 site phosphorylation or genetically mimicking ser184 site phosphorylation (i.e. S184E) results in abrogation of BAX's proapoptotic function.

Effect of Small Molecules that Structurally Target the Ser184 Site of BAX on Apoptosis of Human Lung Cancer Cells or Primary Normal Small Airway Epithelial Cells (SAEC).

Figure 2:
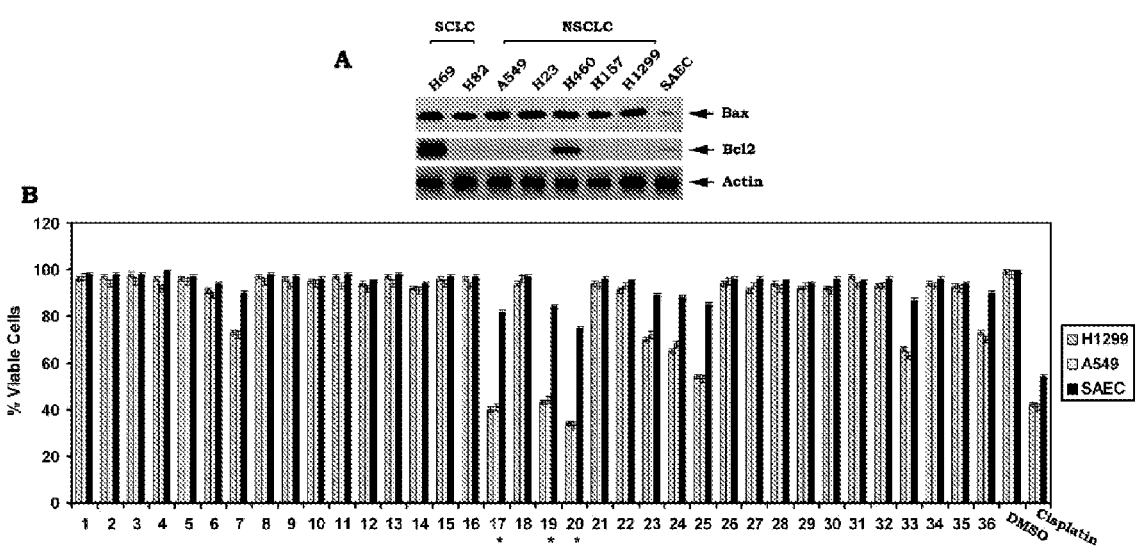
FIG. 2 shows data on the effect of small molecules that structurally target the Ser184 site of BAX on apoptosis of human lung cancer cells. (A) Expression of BAX or Bcl2 in various lung cancer cell lines or primary normal small airway epithelial cells (SAEC) was analyzed by Western blot. (B) H1299, A549 or SAEC cells were treated with various types of small molecules (1 μM) for 48 h. Cell viability was assessed using ApoAlert Annexin-V kit. DMSO or cisplatin (40 μM) was used as a negative or positive control, respectively.

Both SCLC and NSCLC cells express high levels of endogenous BAX (FIG. 2A). In contrast, normal small airway epithelial cells (SAEC) express a relatively low level of endogenous BAX (FIG. 2A). These preliminary data suggest that BAX may be an ideal therapeutic target in human lung cancers. To test whether small molecules that target BAX at the Ser184 site induce apoptosis, H1299, A549 or SAEC cells were treated with various small molecules (1 µM) for 48 h. The compound 2-(2-Nitro-fluoren-9-ylidenemethyl)-phenol (17) has a potent apoptotic effect on human lung cancer H1299 or A549 cells as compared to the other small molecules tested (FIG. 2B) and a significantly less apoptotic effect on normal small airway epithelial cells that express relative low level of BAX as compared to H1299 or A549 cells (FIG. 2B).

Compounds Prevent Nicotine-Induced BAX Phosphorylation

A549 cells were metabolically labeled with $^{32}$P-orthophosphoric acid and treated with nicotine in the absence or presence of 2-(2-Nitro-fluoren-9-ylidenemethyl)-phenol, 2 or 3 for 60 min. Treatment suppresses nicotine-induced BAX phosphorylation. Functionally, nicotine can prolong survival of A549 cells following treatment with the therapeutic drug cisplatin but failed to enhance survival after treatment of cells with 2-(2-Nitro-fluoren-9-ylidenemethyl)-phenol, suggesting that inhibition of BAX phosphorylation can bock nicotine's survival activity. The compound, 2-(2-Nitro-fluoren-9-ylidenemethyl)-phenol, in combination with cisplatin enhances apoptotic cell death suggesting BAX agonists in combination with chemotherapeutics for treating patients with lung cancer.

Figure 3:
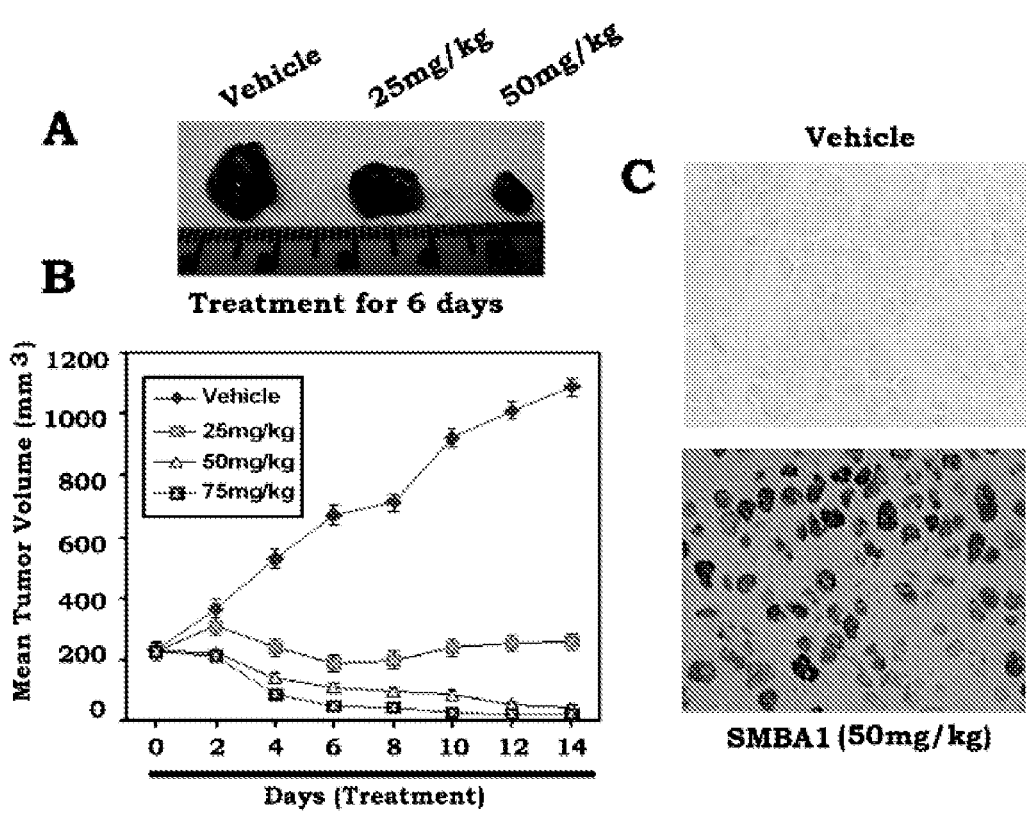
FIG. 3 shows data suggesting in vivo anti-tumor activity of 2-(2-Nitro-fluoren-9-ylidenemethyl)-phenol. (A) A549 lung cancer xenografts were administered intraperitoneally (q.d.) with vehicle control or 2-(2-Nitro-fluoren-9-ylidenemethyl) phenol (SMBA1) as indicated doses. At day 6, tumors were removed and photographed. (B) A549 lung cancer xenograft mice were treated with vehicle control or increasing doses of 2-(2-Nitro-fluoren-9-ylidenemethyl)-phenol (i.e. 25 mg/kg, 50 mg/kg, or 75 mg/kg) for 14 days. Tumor volume was estimated by caliper measurements, data are mean±s.e.m. (C) Mice with xenografts were treated with vehicle or 2-(2-Nitro-fluoren-9-ylidenemethyl)phenol (50 mg/kg) for 24 h. Apoptosis in tumor tissues was measured by TUNEL assay.
Figure 4:
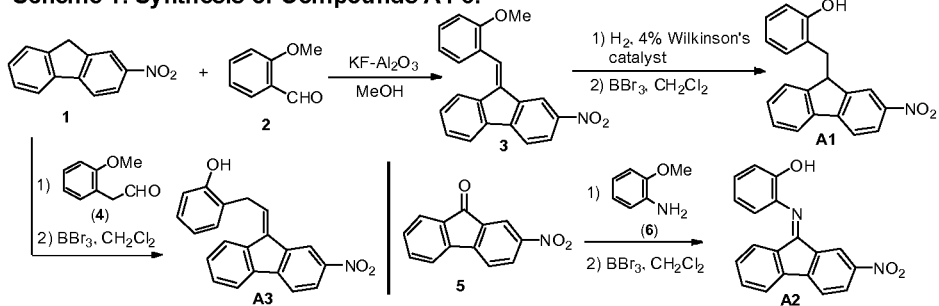
FIG. 4 schematically illustrates methods for preparing compounds disclosed herein.
Figure 4:
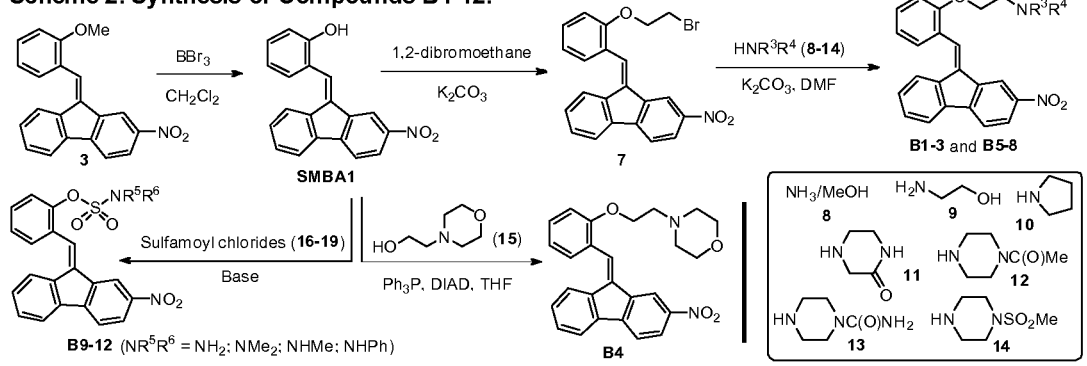
Figure 4:
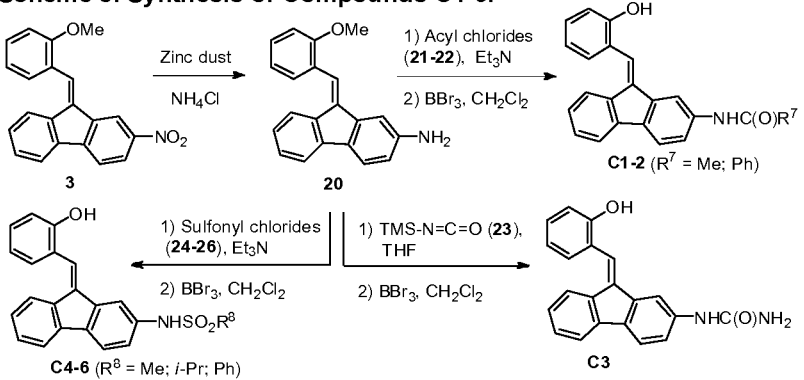
Figure 4:
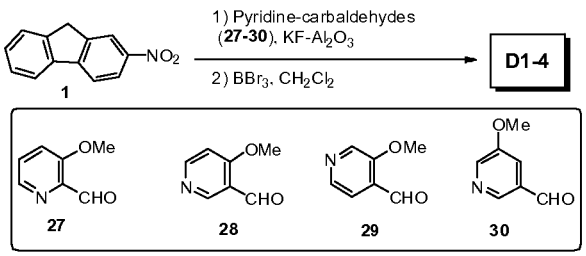

To test whether 2-(2-Nitro-fluoren-9-ylidenemethyl)-phenol actually works in vivo, the anti-lung cancer efficacy of was tested using nude mice to produce subcutaneous (s.c.) lung tumor xenografts as described. Five-week-old Nu/Nu nude mice were purchased from Harlan. $5 \times 10^6$ of A549 cells in a balanced salt solution were injected into s.c. tissue at the flank region of nude mice. The tumors were allowed to grow to an average volume of 225-230 mm$^3$ prior to initiation of therapy as described. Three various doses of 2-(2-Nitro-fluoren-9-ylidenemethyl)-phenol (25 mg/kg, 50 mg/kg or 75 mg/kg) were administered intraperitoneally (i.p.) to mice each day (q.d.) for two weeks (n=8 mice). 0.5% DMSO vehicle was used as a control (n=8 mice). Tumor volume was estimated by caliper measurements (V=L×W2/2). Preliminary results show that treatments doses were well tolerated and caused significant regression of established lung cancer xenografts (FIGS. 3A&B). Importantly, doses of 50-75 mg/kg are well tolerated without significant toxicities on liver, kidney and heart.

To test whether 2-(2-Nitro-fluoren-9-ylidenemethyl)-phenol induces apoptosis in vivo, mice with lung cancer were treated with vehicle control or 50 mg/kg for 24 h. Apoptosis in tumor tissues was analyzed by TUNEL assay. Intriguingly, treatment of lung cancer xenograft mice with 2-(2-Nitro-fluoren-9-ylidenemethyl)-phenol resulted in apoptosis in tumor tissues (FIG. 3C).

Synthetic Methods

2-Methoxy-3-(2-nitro-fluoren-9-ylidenemethyl)-pyridine (CYD-1-76)

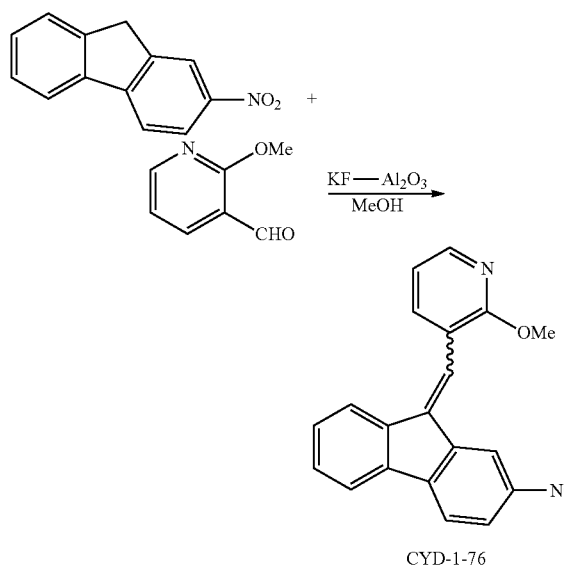

To a solution of 2-nitrofluorene (278 mg, 1.32 mmol) and 2-methoxy-3-pyridinecarboxyaldehyde (200 mg, 1.46 mmol) in 15 mL of methanol was added KF—Al$_2$O$_3$ (190 mg, 1.18 mmol). The resulting mixture was stirred at 72° C. After 8 hrs, TLC indicated that the starting material was gone. 40 mL of CH$_2$Cl$_2$ was added into the reaction mixture. The insoluble solid was filtrated, and the filtrate was concentrated under vacuum to give a yellow solid, which was recrystallized from alcohol and CH$_2$Cl$_2$ to give 306 mg of CYD-1-76 as a yellow solid. $^1$H-NMR (600 MHz, CDCl$_3$) δ 8.88 (s, 1H), 8.32 (m, 10H), 8.10 (m, 22H), 8.01 (d, 1H, J=7.2 Hz), 7.94 (s, 3H), 7.53 (m, 7H), 7.48 (m, 1H), 7.43 (d, 1H, J=7.8 Hz), 7.31 (m, 1H), 7.19 (m, 4H), 3.94 (s, 14H).

9-(2-Methoxy-benzylidene)-2-nitro-9H-fluorene (CYD-1-70)

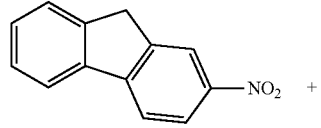

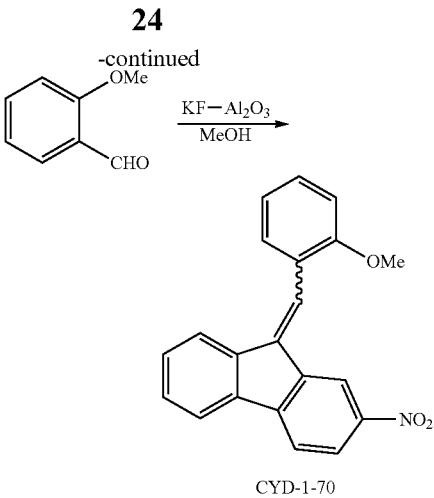

To a solution of 2-nitrofluorene (1.05 g, 5 mmol) and 2-methoxybenzaldehyde (0.816 g, 6 mmol) in 20 mL of methanol was added KF—Al$_2$O$_3$ (0.75 g, 4.5 mmol). The resulting mixture was stirred at 72° C. After 6 hrs, TLC indicated that the starting material was gone. 40 mL of CH$_2$Cl$_2$ was added into the reaction mixture. The insoluble solid was filtrated, and the filtrate was concentrated under vacuum to give a yellow solid, which was recrystallized from alcohol and CH$_2$Cl$_2$ to give 1.2 g of CYD-1-70 as a yellow solid. $^1$H-NMR (600 MHz, CDCl$_3$) δ 8.84 (s, 0.36H), 8.26 (m, 1.65H), 8.10 (m, 3.05H), 8.02 (s, 0.57H), 7.55 (m, 4H), 7.24 (m, 1.24H), 7.10 (m, 0.91H), 3.84 (s, 3H)

2-(2-Nitro-fluoren-9-ylidenemethyl)-phenol (CYD-1-87)

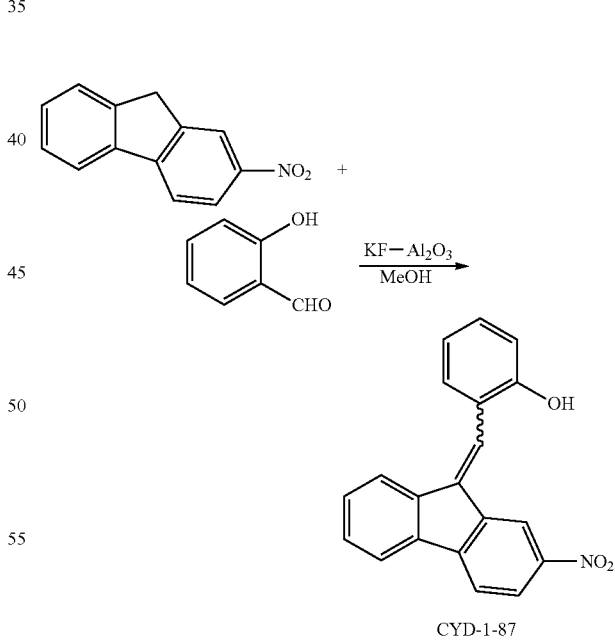

To a solution of 2-nitrofluorene (250 mg, 1.18 mmol) and salicylaldehyde (159 mg, 1.30 mmol) in 10 mL of methanol was added KF—Al$_2$O$_3$ (170 mg, 1.06 mmol). The resulting mixture was stirred at 72° C. After 6 hrs, TLC indicated that the starting material was gone. 40 mL of CH$_2$Cl$_2$ was added into the reaction mixture. The insoluble solid was filtrated, and the filtrate was concentrated under vacuum to give a yellow solid, which was purified by silica gel column; eluting with 11% EtOAc in hexane afforded 125 mg of CYD-1-87 as a yellow solid. ¹H-NMR (600 MHz, CDCl₃) δ 10.05 (br s, 1H), 8.39 (s, 1H), 8.27 (dd, 1H, J=2.4 Hz, 8.4 Hz), 8.16 (d, 1H, J=8.4 Hz), 8.09 (m, 2H), 8.04 (s, 1H), 7.52 (m, 3H), 7.37 (m, 1H), 7.05 (d, 1H, J=8.4 Hz), 6.96 (t, 1H, J=7.2 Hz).

2-Methoxy-3-(2-nitro-fluoren-9-ylidenemethyl)-pyridine (CYD-1-76)

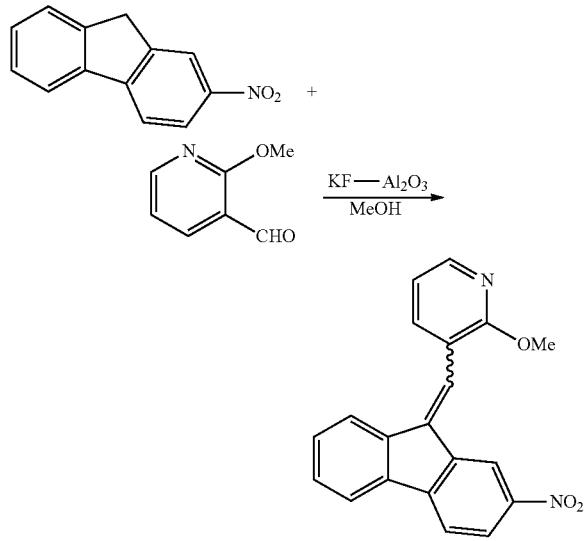

CYD-1-76

To a solution of 2-nitrofluorene (278 mg, 1.32 mmol) and 2-methoxy-3-pyridinecarboxyaldehyde (200 mg, 1.46 mmol) in 15 mL of methanol was added KF—Al₂O₃ (190 mg, 1.18 mmol). The resulting mixture was stirred at 72° C. After 8 hrs, TLC indicated that the starting material was gone. 40 mL of CH₂Cl₂ was added into the reaction mixture. The insoluble solid was filtered, and the filtrate was concentrated under vacuum to give a yellow solid, which was recrystallized from alcohol and CH₂Cl₂ to give 306 mg of CYD-1-76 as a yellow solid. ¹H-NMR (600 MHz, CDCl₃) δ 8.88 (s, 1H), 8.32 (m, 10H), 8.10 (m, 22H), 8.01 (d, 1H, J=7.2 Hz), 7.94 (s, 3H), 7.53 (m, 7H), 7.48 (m, 1H), 7.43 (d, 1H, J=7.8 Hz), 7.31 (m, 1H), 7.19 (m, 4H), 3.94 (s, 14H).

9-(2-Methoxy-benzylidene)-2-nitro-9H-fluorene (CYD-1-70)

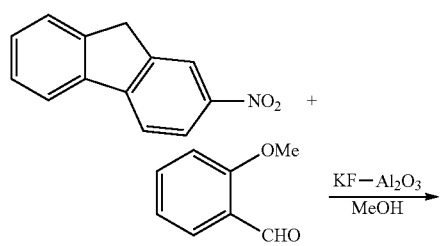

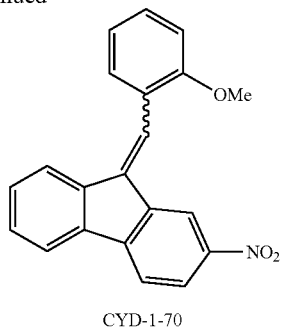

CYD-1-70

To a solution of 2-nitrofluorene (1.05 g, 5 mmol) and 2-methoxybenzaldehyde (0.816 g, 6 mmol) in 20 mL of methanol was added KF—Al₂O₃ (0.75 g, 4.5 mmol). The resulting mixture was stirred at 72° C. After 6 hrs, TLC indicated that the starting material was gone. 40 mL of CH₂Cl₂ was added into the reaction mixture. The insoluble solid was filtrated, and the filtrate was concentrated under vacuum to give a yellow solid, which was recrystallized from alcohol and CH₂Cl₂ to give 1.2 g of CYD-1-70 as a yellow solid. ¹H-NMR (600 MHz, CDCl₃) δ 8.84 (s, 0.36H), 8.26 (m, 1.65H), 8.10 (m, 3.05H), 8.02 (s, 0.57H), 7.55 (m, 4H), 7.24 (m, 1.24H), 7.10 (m, 0.91H), 3.84 (s, 3H). ¹³C-NMR (150 MHz, CDCl₃) δ 157.7, 147.4, 146.6, 146.5, 144.2, 140.8, 140.0, 138.6, 137.9, 136.8, 136.6, 134.2, 134.0, 131.5, 131.2, 131.1, 130.8, 129.6, 129.5, 129.2 (2C), 128.9, 128.4, 124.5, 124.3, 124.2, 124.1, 123.9, 122.2, 121.9, 121.6, 121.1, 120.9, 120.8 (2C), 119.1, 116.6 (2C), 112.1, 112.0, 55.9 (2C).

3-((2-Nitro-9H-fluoren-9-ylidene)methyl)pyridin-2(1H)-one (CYD-1-93)

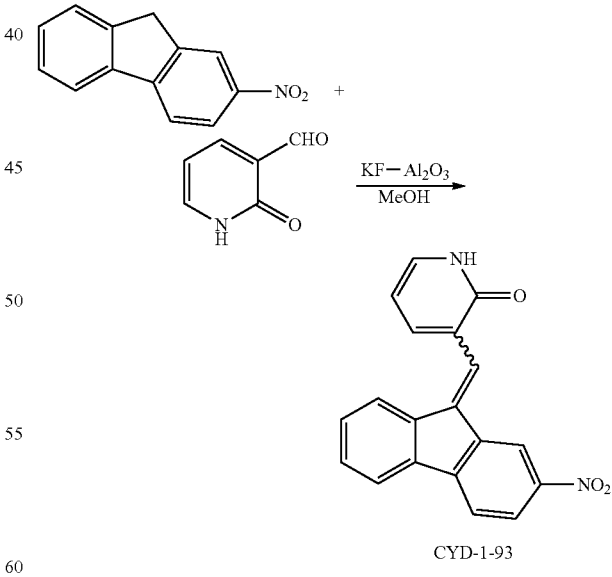

CYD-1-93

To a solution of 2-nitrofluorene (326 mg, 1.54 mmol) and 2-oxo-1,2-dihydro-pyridine-3-carbaldehyde (19 mg, 1.54 mmol) in 10 mL of methanol was added KF—Al₂O₃ (224 mg, 1.38 mmol). The resulting mixture was stirred at 85° C. After 24 hrs, TLC indicated that a new product was produced and lots of starting material was still remained. 40 mL of CH₂Cl₂ was added into the reaction mixture. The insoluble solid was filtrated, and the filtrate was concentrated under vacuum to give a yellow solid, which was purified by silica gel column; eluting with 60% EtOAc in hexane afforded 26 mg of CYD-1-93 as a yellow solid. $^1$H-NMR (600 MHz, d$_6$-DMSO) δ 12.18 (br s, 2H), 8.77 (d, 1H, J=1.8 Hz), 8.52 (d, 1H, J=1.8 Hz), 8.28 (m, 2H), 8.15 (m, 2H), 8.10 (d, 1H, J=7.8 Hz), 8.06 (m, 2H), 7.97 (m, 2H), 7.86 (m, 2H), 7.80 (s, 1H), 7.63 (m, 1H), 7.59 (m, 1H), 7.49 (m, 3H), 7.37 (m, 1H), 6.40 (m, 2H). $^{13}$C-NMR (150 MHz, CDCl$_3$) δ 161.2, 161.1, 146.9, 146.2, 146.1, 143.6, 142.1, 141.7, 140.5, 139.6, 138.3, 137.3, 136.1, 136.0, 133.6, 133.4, 129.3, 129.1, 129.0, 128.8, 127.9, 127.4, 126.1, 125.9, 124.0, 123.9, 123.5, 121.9, 121.5, 121.1, 120.7, 120.5, 119.0, 105.1, 105.0.

9-(2-Methoxy-benzylidene)-9H-fluoren-2-ylamine (CYD-1-96)

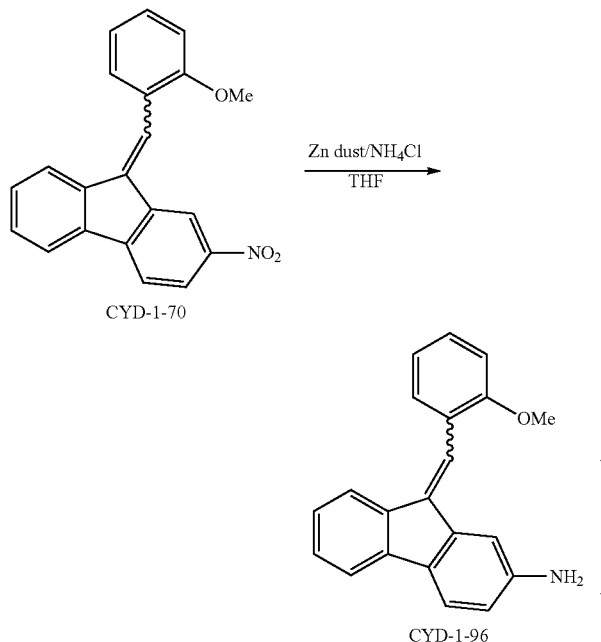

To a solution of CYD-1-70 (100 mg, 0.304 mmol) in 10 mL of THF was added 0.4 mL of sat. NH$_4$Cl and 0.4 mL of H$_2$O. The resulting mixture was cooled to 0° C. in an ice-water bath. Then 236 mg of Zinc dust was added into it at 0° C. The reaction was stirred at rt for 2 hrs. TLC indicated that the starting material was gone. The Zinc solid was filtrated, and the filtrate was concentrated under vacuum to give a yellow residue, which was purified by silica gel column; eluting with 33% EtOAc in hexane afforded 90 mg of CYD-1-96 (100%) as yellow oil. One isomer: $^1$H-NMR (600 MHz, CDCl$_3$) δ 7.71 (d, 1H, J=7.2 Hz), 7.62 (m, 2H), 7.51 (m, 1H), 7.42 (m, 1H), 7.33 (m, 1H), 7.26 (m, 1H), 7.18 (m, 1H), 6.94 (m, 3H), 6.56 (m, 1H), 3.80 (s, 3H); Another isomer: 7.62 (m, 1H), 7.54 (s, 1H), 7.51 (m, 2H), 7.42 (m, 1H), 7.33 (m, 1H), 7.18 (m, 2H), 7.04 (d, 1H, J=1.8 Hz), 6.94 (m, 2H), 6.64 (m, 1H), 3.80 (s, 3H). $^{13}$C-NMR (150 MHz, CDCl$_3$) δ 157.7, 157.6, 146.0, 145.5, 141.9, 141.4, 139.7, 139.1, 138.4, 136.3, 136.3, 136.2, 132.7, 131.2, 131.2, 130.6, 129.8, 129.8, 128.3, 128.0, 125.6, 125.6, 125.3, 124.9, 124.1, 123.5, 123.3, 120.4, 120.3, 120.3, 120.3, 120.2, 118.4, 118.2, 115.5, 115.3, 111.1, 110.8, 110.8, 107.2, 55.5, 55.5.

4-{2-[2-(2-Nitro-fluoren-9-ylidenemethyl)-phenoxy]-ethyl}-morpholine (CYD-1-95)

To a solution of CYD-1-94 (80 mg, 0.25 mmol) in 8 mL of THF was added PPh$_3$ (117.9 mg, 0.45 mmol) and 2-morpholin-4-yl-ethanol (59 mg, 0.45 mmol). Then DIAD (91 mg, 0.45 mmol) was added into the resulting mixture. The reaction mixture was stirred at rt for 3 hrs. After that, TLC showed CYD-1-94 was gone. The solvent was removed under vacuum to give a yellow residue, which was purified by silica gel column; eluting with EtOAc afforded 87 mg of CYD-1-93 as yellow oil. $^1$H-NMR (600 MHz, CDCl$_3$) δ 8.63 (d, 1H, J=1.8 Hz), 8.41 (d, 1H, J=1.8 Hz), 8.25 (dd, 1H, J=1.8 Hz, 8.4 Hz), 8.19 (dd, 1H, J=1.8 Hz, 7.8 Hz), 7.85 (m, 3H), 7.80 (m, 4H), 7.67 (d, 1H, J=7.8 Hz), 7.63 (d, 1H, J=7.2 Hz), 7.58 (d, 1H, J=6.6 Hz), 7.41 (m, 5H), 7.19 (m, 1H), 7.10 (m, 1H), 7.04 (m, 3H), 4.19 (m, 4H), 3.58 (m, 8H), 2.76 (t, 2H, J=6.0 Hz), 2.71 (t, 2H, J=6.0 Hz), 2.48 (s, 8H). $^{13}$C-NMR (150 MHz, CDCl$_3$) δ 156.9, 156.8, 147.0, 146.3, 144.3, 141.0, 140.2, 138.7, 138.2, 137.1, 136.7, 134.4, 134.2, 130.8, 130.8, 130.8, 130.5, 128.8, 128.7, 128.5, 128.4, 127.0, 124.8, 124.5, 124.4, 123.6, 123.3, 120.9, 120.8, 120.8, 120.6, 120.5, 119.7, 119.5, 119.4, 115.8, 112.2, 112.1, 66.8, 66.7, 66.7, 66.7, 57.4 (2C), 54.0 (6C).

1-{2-[2-(2-Nitro-fluoren-9-ylidenemethyl)-phenoxy]-ethyl}-piperazine (CYD-2-7-1)

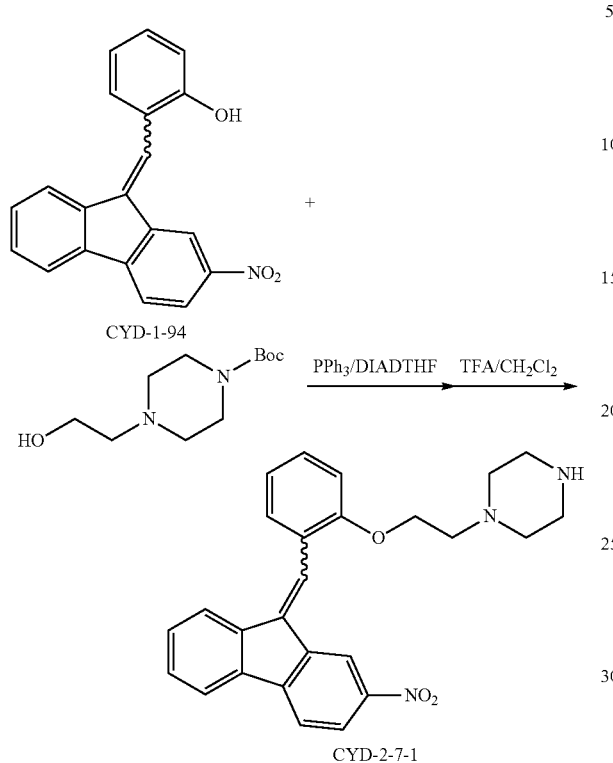

To a solution of CYD-1-94 (120 mg, 0.38 mmol) in 8 mL of THF was added PPh$_3$ (179 mg, 0.68 mmol) and 4-(2-hydroxy-ethyl)-piperazine-1-carboxylic acid tert-butyl ester (157 mg, 0.68 mmol). Then DIAD (138 mg, 0.68 mmol) was added into the resulting mixture. The reaction mixture was stirred at rt for 3 hrs. After that, TLC showed CYD-1-94 was gone. The solvent was removed under vacuum to give a yellow residue, which was purified by silica gel column; eluting with 50% EtOAc in hexane afforded 196 mg of CYD-2-7 as yellow oil. CYD-2-7 (196 mg, 0.37 mmol) was dissolved in 4 mL of CH$_2$Cl$_2$, and then 1 mL of TFA was added into it at 0° C. The resulting mixture was stirred at rt for 4 hrs. After that, TLC showed that CYD-2-7 disappeared. The reaction mixture was washed with sat. NaHCO$_3$, and concentrated under vacuum to give an oil residue, which was purified by silica gel column; eluting with CH$_2$Cl$_2$/MeOH/Et$_3$N=10:1:0.3 afforded 160 mg of CYD-2-7-1 as yellow oil. $^1$H-NMR (600 MHz, CDCl$_3$) δ 8.57 (s, 1H), 8.37 (s, 1H), 8.13 (m, 2H), 7.82 (m, 3H), 7.70 (m, 4H), 7.65 (d, 1H, J=7.8 Hz), 7.59 (d, 1H, J=7.2 Hz), 7.55 (d, 1H, J=7.2 Hz), 7.41 (m, 4H), 7.33 (t, 1H, J=7.2 Hz), 7.16 (t, 1H, J=7.2 Hz), 7.07 (m, 1H), 7.02 (m, 3H), 4.82 (br s, 2H), 4.17 (m, 4H), 2.82 (m, 8H), 2.76 (t, 2H, J=6.0 Hz), 2.71 (t, 2H, J=5.4 Hz), 2.53 (m, 8H). $^{13}$C-NMR (150 MHz, CDCl$_3$) δ 156.8 (2C), 146.8, 146.5, 146.2, 144.1, 140.9, 140.1, 138.5, 138.0, 136.9, 136.6, 134.2, 134.0, 130.9, 130.8 (2C), 130.6, 128.8, 128.7, 128.5, 128.3, 127.0 (2C), 124.6, 124.3, 123.5 (2C), 123.2, 120.9, 120.8, 120.7, 120.5 (2C), 119.6 (2C), 119.4 (2C), 115.7, 112.1, 112.0, 66.6, 66.5, 57.3, 57.2, 53.6 (2C), 45.2 (6C).

2-[2-(2-Nitro-fluoren-9-ylidenemethyl)-phenoxy]-ethanol (CYD-2-1)

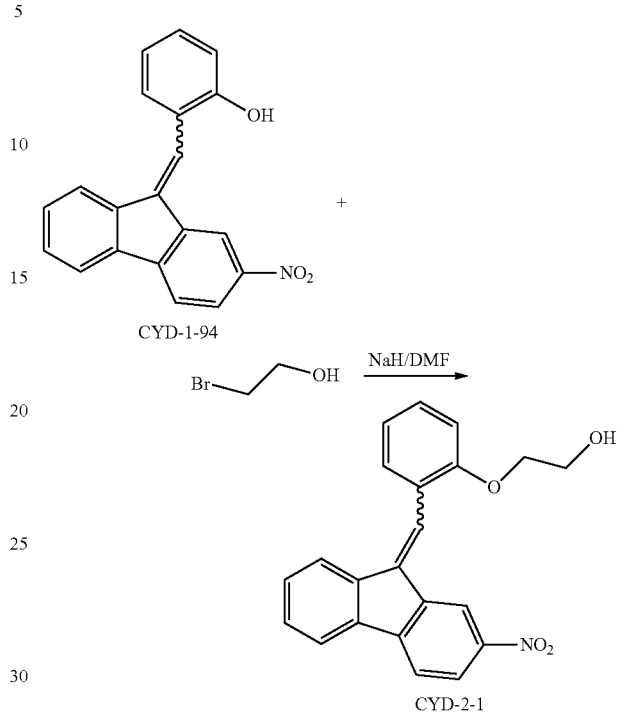

To a solution of CYD-1-94 (120 mg, 0.38 mmol) in 8 mL of DMF was added NaH (12 mg, 0.49 mmol). The color of mixture turned into dark red. After 5 min, 2-bromoethanol (142 mg, 1.14 mmol) was added into the resulting mixture. The reaction was stirred at 60° C. for 24 hrs. After that, TLC showed most of CYD-1-94 was gone. The DMF solvent was removed at 60° C. under vacuum to give a yellow oil residue, which was purified by silica gel column; eluting with 80% EtOAc in hexane afforded 86 mg of CYD-2-1 as a yellow solid. $^1$H-NMR (600 MHz, CDCl$_3$) δ 8.84 (d, 1H, J=1.2 Hz), 8.34 (d, 1H, J=1.8 Hz), 8.31 (dd, 1H, J=1.8 Hz, 8.4 Hz), 8.27 (dd, 1H, J=1.8 Hz, 7.8 Hz), 8.17 (m, 3H), 8.09 (m, 4H), 7.62 (m, 3H), 7.53 (m, 3H), 7.48 (m, 2H), 7.29 (t, 1H, J=7.8 Hz), 7.23 (m, 2H), 7.10 (m, 2H), 4.86 (t, 1H, J=5.4 Hz), 4.82 (t, 1H, J=5.4 Hz), 4.11 (m, 4H), 3.66 (m, 4H).

2-[2-(2-Nitro-fluoren-9-ylidenemethyl)-phenoxy]-ethylamine (CYD-2-11)

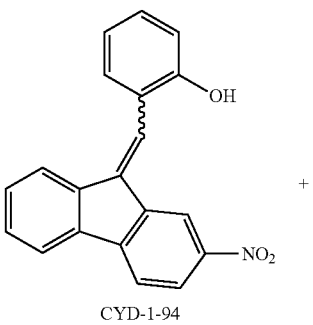

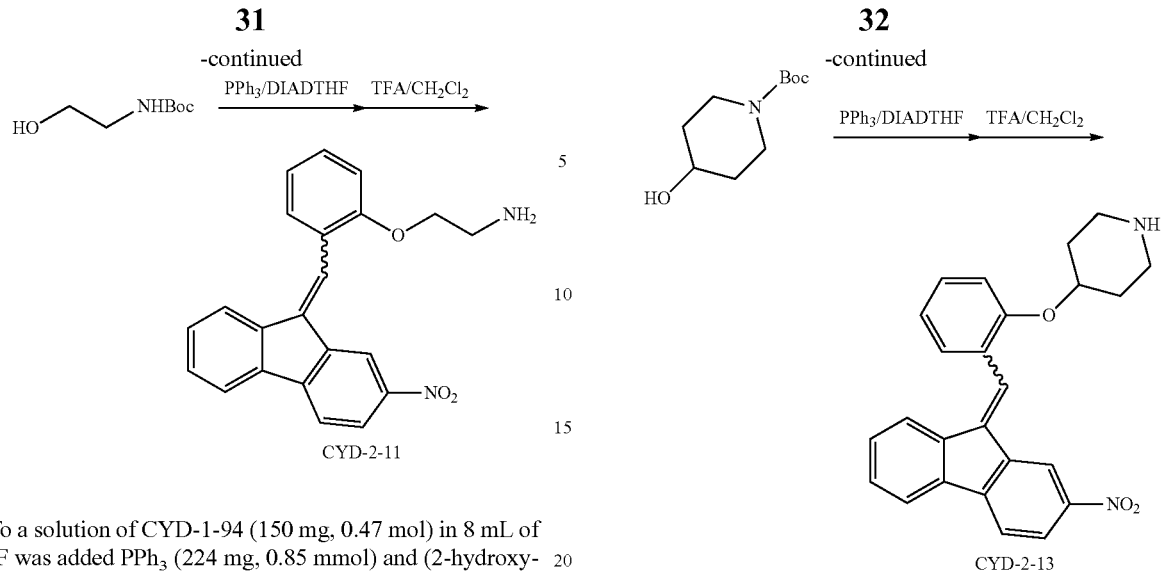

To a solution of CYD-1-94 (150 mg, 0.47 mol) in 8 mL of THF was added PPh₃ (224 mg, 0.85 mmol) and (2-hydroxyethyl)-carbamic acid tert-butyl ester (138 mg, 0.85 mmol). Then DIAD (173 mg, 0.85 mmol) was added into the resulting mixture. The reaction mixture was stirred at rt for 4 hrs. After that, TLC showed CYD-1-94 was gone. The solvent was removed under vacuum to give a yellow residue, which was purified by silica gel column; eluting with 80% EtOAc in hexane afforded 160 mg of CYD-2-10 as yellow oil. CYD-2-10 (160 mg, 0.34 mmol) was dissolved in 4 mL of CH₂Cl₂, and then 1 mL of TFA was added into it at 0° C. The resulting mixture was stirred at rt for 4 hrs. After that, TLC showed that CYD-2-10 disappeared. The reaction mixture was washed with sat. NaHCO₃, and concentrated under vacuum to give an oil residue, which was purified by silica gel column; eluting with CH₂Cl₂/MeOH/Et₃N=10:1:0.3 afforded 125 mg of CYD-2-7-1 as yellow oil. ¹H-NMR (600 MHz, CDCl₃) δ 8.66 (d, 2H, J=1.8 Hz), 8.43 (d, 2H, J=1.8 Hz), 8.26 (dd, 2H, J=1.8 Hz, 8.4 Hz), 8.20 (dd, 1H, J=1.8 Hz, 9.0 Hz), 7.91 (m, 2H), 7.86 (s, 2H), 7.80 (m, 6H), 7.67 (d, 2H, J=7.8 Hz), 7.63 (d, 2H, J=7.8 Hz), 7.60 (d, 1H, J=7.8 Hz), 7.44 (m, 7H), 7.21 (t, 2H, J=7.8 Hz), 7.07 (m, 6H), 4.10 (m, 6H), 3.04 (br s, 6H), 2.66 (m, 6H). ¹³C-NMR (150 MHz, CDCl₃) δ 156.6, 146.9, 146.5, 146.3, 144.3, 140.9, 140.1, 138.6, 138.1, 137.0, 136.6, 134.4 (2C), 131.0 (2C), 130.9, 130.6, 128.9, 128.8, 128.5, 128.4, 126.7 (2C), 124.6, 124.4, 124.3, 123.6, 123.3, 120.9 (2C), 120.8, 120.7, 120.6, 119.6, 119.5 (2C), 115.9, 112.1, 112.0, 69.9, 40.8.

4-[2-(2-Nitro-fluoren-9-ylidenemethyl)-phenoxy]-piperidine (CYD-2-13)

To a solution of CYD-1-94 (155 mg, 0.49 mol) in 8 mL of THF was added PPh₃ (232 mg, 0.88 mmol) and 4-hydroxy-piperidine-1-carboxylic acid tert-butyl ester (178 mg, 0.88 mmol). Then DIAD (178 mg, 0.88 mmol) was added into the resulting mixture. The reaction mixture was stirred at rt for 4 hrs. After that, TLC showed CYD-1-94 was gone. The solvent was removed under vacuum to give a yellow residue, which was purified by silica gel column; eluting with 25% EtOAc in hexane afforded 210 mg of CYD-2-12 as yellow oil. CYD-2-12 (210 mg, 0.42 mmol) was dissolved in 4 mL of CH₂Cl₂, and then 1 mL of TFA was added into it at 0° C. The resulting mixture was stirred at rt for 4 hrs. After that, TLC showed that CYD-2-12 disappeared. The reaction mixture was washed with sat. NaHCO₃, and concentrated under vacuum to give an oil residue, which was purified by silica gel column; eluting with CH₂Cl₂/MeOH/Et₃N=15:1:0.3 afforded 140 mg of CYD-2-13 as yellow oil. ¹H-NMR (600 MHz, CDCl₃) δ 8.57 (s, 1H), 8.40 (s, 1H), 8.18 (d, 1H, J=8.4 Hz), 8.12 (d, 1H, J=7.8 Hz), 7.86 (m, 2H), 7.80 (s, 1H), 7.72 (m, 4H), 7.59 (m, 3H), 7.41 (m, 4H), 7.33 (t, 1H, J=7.2 Hz), 7.16 (m, 1H), 7.06 (t, 1H, J=7.2 Hz), 7.02 (m, 3H), 5.79 (br s, 2H), 4.53 (m, 2H), 3.06 (m, 4H), 2.81 (m, 4H), 2.03 (m, 4H), 1.79 (m, 4H). ¹³C-NMR (150 MHz, CDCl₃) δ 155.3, 155.2, 147.0, 146.6, 146.4, 144.3, 140.9, 140.1, 138.7, 138.1, 136.9, 136.6, 134.4 (2C), 131.3, 131.2, 130.7, 130.4, 128.9, 128.8, 128.5, 128.4, 126.8, 125.9, 125.5, 124.4, 123.6, 123.3, 121.1, 120.9 (2C), 120.8, 120.6, 119.6, 119.5, 119.4, 115.7, 114.1 (2C), 72.3, 71.8, 42.2 (2C), 42.0 (2C), 30.3 (2C), 30.0 (2C).

1-(4-Fluoro-benzenesulfonyl)-4-{2-[2-(2-nitro-fluoren-9-ylidenemethyl)-phenoxy]-ethyl}-piperazine (CYD-2-18)

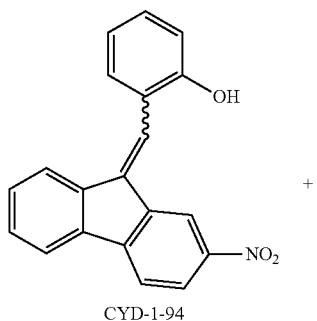

CYD-1-94

+

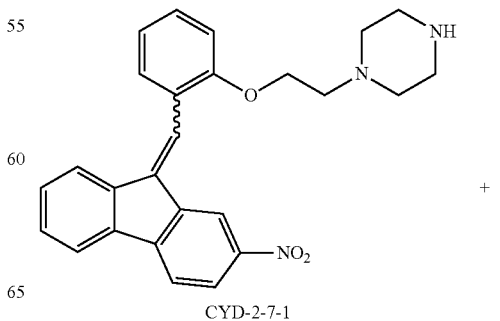

CYD-2-7-1

+

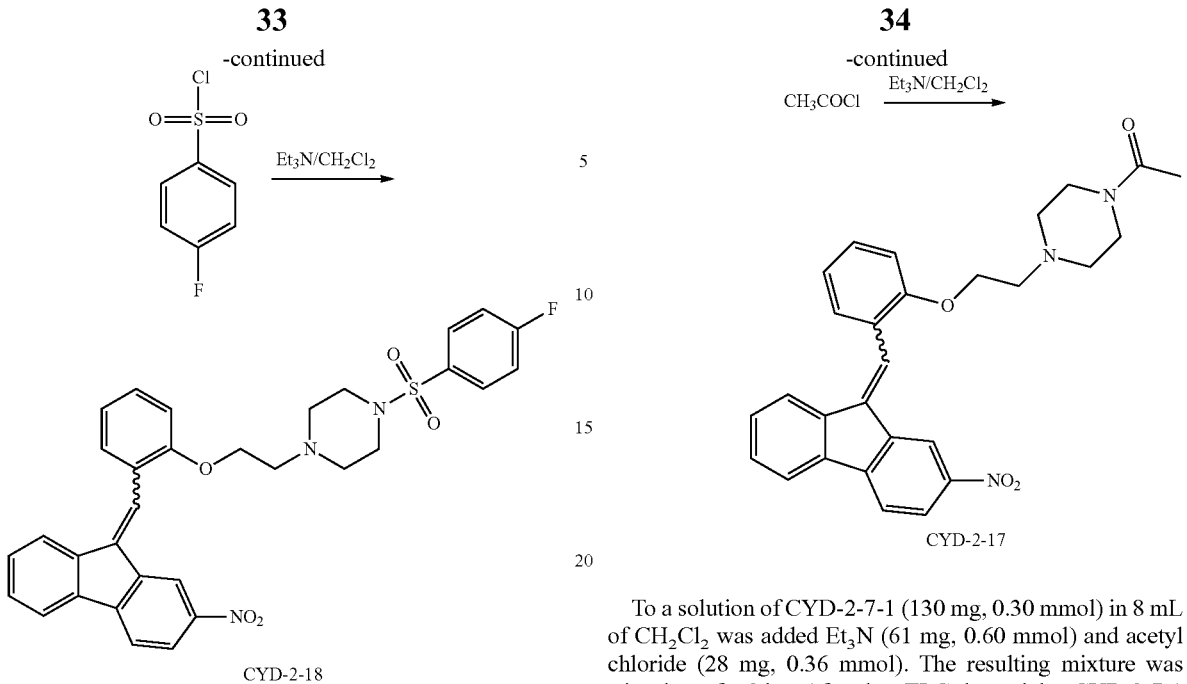

To a solution of CYD-2-7-1 (120 mg, 0.28 mmol) in 8 mL of CH$_2$Cl$_2$ was added Et$_3$N (56.8 mg, 0.56 mmol) and 4-fluoro-benzenesulfonyl chloride (65 mg, 0.33 mmol). The resulting mixture was stirred at rt for 2 hrs. After that, TLC showed that CYD-2-7-1 was gone. The reaction mixture was washed with water, and dried with anhydrous Na$_2$SO$_4$. The solvent was removed under vacuum to give a yellow oil residue, which was purified by silica gel column; eluting with 50% EtOAc in hexane afforded 101 mg of CYD-2-18 as a yellow solid. $^1$H-NMR (600 MHz, CDCl$_3$) δ 8.56 (d, 1H, J=1.2 Hz), 8.17 (dd, 1H, J=1.2 Hz, 7.8 Hz), 7.78 (s, 1H), 7.76 (d, 1H, J=7.2 Hz), 7.71 (d, 1H, J=8.4 Hz), 7.62 (m, 2H), 7.56 (d, 2H, J=7.8 Hz), 7.36 (m, 2H), 7.14 (m, 1H), 7.03 (m, 3H), 6.96 (m, 1H). 4.10 (m, 2H), 2.83 (s, 4H), 2.73 (t, 2H, J=5.4 Hz), 2.51 (m, 4H); $^{13}$C-NMR (150 MHz, CDCl$_3$) δ 166.0, 164.3, 156.7, 156.6, 147.1, 146.7, 146.3, 144.2, 140.9, 140.1, 138.7, 138.1, 137.1, 136.7, 134.5 (2C), 134.4, 131.6 (2C), 130.8 (2C), 130.5, 130.3 (2C), 128.9, 128.8, 128.6, 128.5, 126.8, 124.8, 124.5 (2C), 124.4, 123.6 (2C), 123.4, 121.0 (2C), 120.9, 120.8, 120.4, 119.7 (2C), 119.6, 119.5, 116.2 (2C), 116.0 (2C), 115.7, 112.2, 112.1, 66.9, 66.7, 56.5 (2C), 52.5 (2C), 45.8 (2C).

1-(4-{2-[2-(2-Nitro-fluoren-9-ylidenemethyl)-phenoxy]-ethyl}-piperazin-1-yl)-ethanone (CYD-2-17)

To a solution of CYD-2-7-1 (130 mg, 0.30 mmol) in 8 mL of CH$_2$Cl$_2$ was added Et$_3$N (61 mg, 0.60 mmol) and acetyl chloride (28 mg, 0.36 mmol). The resulting mixture was stirred at rt for 2 hrs. After that, TLC showed that CYD-2-7-1 was gone. The reaction mixture was washed with water, and dried with anhydrous Na$_2$SO$_4$. The solvent was removed under vacuum to give a yellow oil residue, which was purified by silica gel column; eluting with CH$_2$Cl$_2$/MeOH=15:1 afforded 108 mg of CYD-2-17 as a yellow oil (75%). $^1$H-NMR (600 MHz, CDCl$_3$) δ 8.61 (s, 1H), 8.37 (s, 1H), 8.22 (m, 1H), 8.18 (m, 1H), 7.84 (s, 3H), 7.78 (m, 4H), 7.66 (d, 1H, J=7.8 Hz), 7.62 (d, 1H, J=7.2 Hz), 7.57 (d, 1H, J=7.8 Hz), 7.44 (m, 4H), 7.37 (m, 1H), 7.19 (m, 1H), 7.09 (m, 1H), 7.03 (m, 3H), 4.18 (m, 4H), 3.49 (s, 4H), 3.29 (d, 2H, J=4.8 Hz), 3.24 (d, 2H, J=4.2 Hz), 2.79 (m, 2H), 2.72 (m, 2H), 2.50 (d, 2H, J=4.2 Hz), 2.43 (m, 6H), 1.97 (s, 3H), 1.96 (s, 3H); $^{13}$C-NMR (150 MHz, CDCl$_3$) δ 168.8, 168.7, 156.8, 156.6, 146.9, 146.6, 146.2, 144.2, 140.9, 140.1, 138.6, 138.1, 137.0, 136.7, 134.4, 134.2, 130.8 (2C), 130.6, 128.9, 128.8, 128.6, 128.5, 127.0 (2C), 124.7, 124.4, 123.6, 123.3 (2C), 120.9 (3C), 119.7 (2C), 119.5 (2C), 115.7, 112.2, 112.0, 66.8, 66.7, 56.8 (2C), 53.6, 53.5, 53.1, 53.0, 46.1, 46.0, 41.2 (2C), 21.1 (2C)

1-Cyclopropanesulfonyl-4-{2-[2-(2-nitro-fluoren-9-ylidenemethyl)-phenoxy]-ethyl}-piperazine (CYD-2-16)

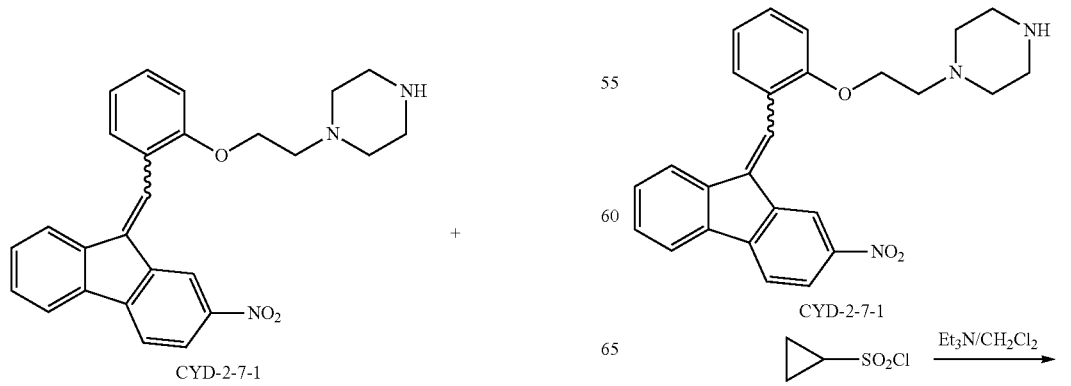

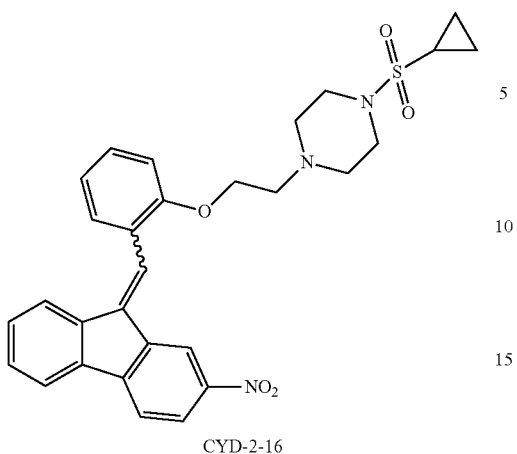

CYD-2-16

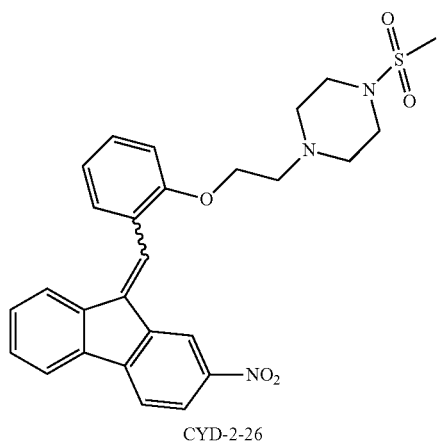

CYD-2-26

To a solution of CYD-2-7-1 (140 mg, 0.32 mmol) in 8 mL of CH$_2$Cl$_2$ was added Et$_3$N (66 mg, 0.65 mmol) and cyclopropanesulfonyl chloride (55 mg, 0.39 mmol). The resulting mixture was stirred at rt for 4 hrs. After that, TLC showed that CYD-2-7-1 was gone. The reaction mixture was washed with water, and dried with anhydrous Na$_2$SO$_4$. The solvent was removed under vacuum to give a yellow oil residue, which was purified by silica gel column; eluting with EtOAc/MeOH=40:1 afforded 109 mg of CYD-2-16 as a yellow solid. $^1$H-NMR (600 MHz, CDCl$_3$) δ 8.64 (d, 1H, J=1.2 Hz), 8.38 (d, 1H, J=1.8 Hz), 8.26 (dd, 1H, J=1.8 Hz, 8.4 Hz), 8.20 (dd, 1H, J=1.8 Hz, 7.8 Hz), 7.87 (m, 3H), 7.81 (m, 4H), 7.66 (m, 2H), 7.58 (d, 1H, J=7.2 Hz), 7.43 (m, 5H), 7.22 (m, 1H), 7.11 (m, 1H), 7.05 (m, 3H), 4.19 (m, 4H), 3.17 (m, 8H), 2.80 (t, 2H, J=6.0 Hz), 2.76 (t, 2H, J=5.4 Hz), 2.57 (m, 8H), 2.17 (m, 2H), 1.09 (m, 4H), 0.91 (m, 4H). $^{13}$C-NMR (150 MHz, CDCl$_3$) δ 156.8, 156.7, 147.1, 146.7, 146.3, 144.3, 140.9, 140.1, 138.7, 138.2, 137.1, 136.7, 134.5, 134.3, 130.8 (3C), 130.5, 128.9, 128.8, 128.5, 126.9, 124.9, 124.5, 124.4, 123.6, 123.4, 121.0 (2C), 120.9, 120.8, 120.4, 119.7 (2C), 119.6, 119.5, 115.7, 112.3, 112.2, 66.8, 66.6, 56.9, 56.6, 52.9 (6C), 45.9 (2C), 25.3, 25.2, 4.2 (2C), 4.1 (2C).

1-Methanesulfonyl-4-{2-[2-(2-nitro-fluoren-9-ylidenemethyl)-phenoxy]-ethyl}-piperazine (CYD-2-26)

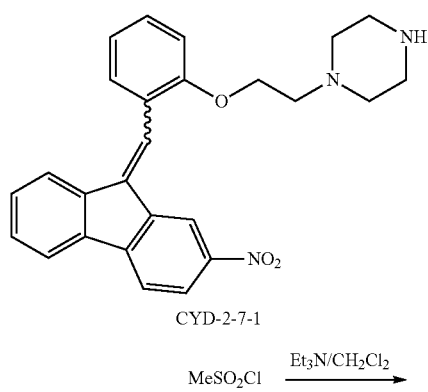

CYD-2-7-1

MeSO$_2$Cl $\xrightarrow{\text{Et}_3\text{N/CH}_2\text{Cl}_2}$

To a solution of CYD-2-7-1 (150 mg, 0.35 mmol) in 8 mL of CH$_2$Cl$_2$ was added Et$_3$N (70 mg, 0.70 mmol) and methanesulfonyl chloride (48 mg, 0.42 mmol). The resulting mixture was stirred at rt for 4 hrs. After that, TLC showed that CYD-2-7-1 was gone. The reaction mixture was washed with water, and dried with anhydrous Na$_2$SO$_4$. The solvent was removed under vacuum to give a yellow oil residue, which was purified by silica gel column; eluting with EtOAc/MeOH=50:1 afforded 130 mg of CYD-2-26 as a yellow solid. $^1$H-NMR (600 MHz, CDCl$_3$) δ 8.58 (d, 1H, J=2.4 Hz), 8.33 (d, 1H, J=2.4 Hz), 8.21 (dd, 1H, J=1.8 Hz, 8.4 Hz), 8.15 (dd, 1H, J=1.8 Hz, 7.8 Hz), 7.82 (m, 3H), 7.76 (m, 4H), 7.64 (d, 1H, J=7.8 Hz), 7.60 (d, 1H, J=7.8 Hz), 7.54 (d, 1H, J=7.2 Hz), 7.39 (m, 5H), 7.17 (t, 1H, J=7.2 Hz), 7.08 (m, 1H), 7.01 (m, 3H), 4.14 (m, 4H), 3.06 (m, 4H), 3.02 (m, 4H), 2.77 (t, 2H, J=5.4 Hz), 2.72 (t, 2H, J=5.4 Hz), 2.65 (s, 3H), 2.63 (s, 3H), 2.53 (m, 8H). $^{13}$C-NMR (150 MHz, CDCl$_3$) δ 156.8, 156.7, 147.0, 146.7, 146.3, 144.3, 140.9, 140.1, 138.7, 138.1, 137.1, 136.7, 134.5, 134.3, 130.9, 130.8 (2C), 130.6, 128.9, 128.8, 128.6, 126.9, 124.9, 124.5, 124.4, 123.6 (2C), 123.4, 121.0, 120.9, 120.8, 120.5, 119.7 (2C), 119.6, 119.5, 115.7, 112.3 (2C), 66.7, 66.5, 56.5 (2C), 52.7 (3C), 52.6 (3C), 45.7 (2C), 34.1, 34.0.

The dimmer of cyclopropanesulfonic acid (9H-fluoren-2-yl)-amide (CYD-2-31)

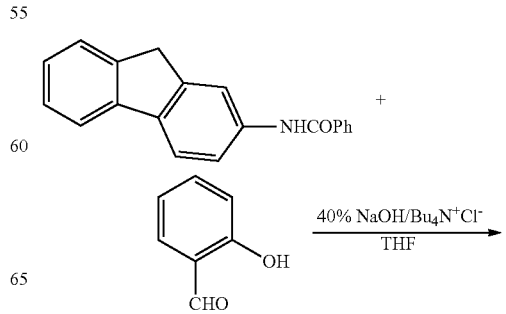

$\xrightarrow[\text{THF}]{\text{40\% NaOH/Bu}_4\text{N}^+\text{Cl}^-}$

37
-continued

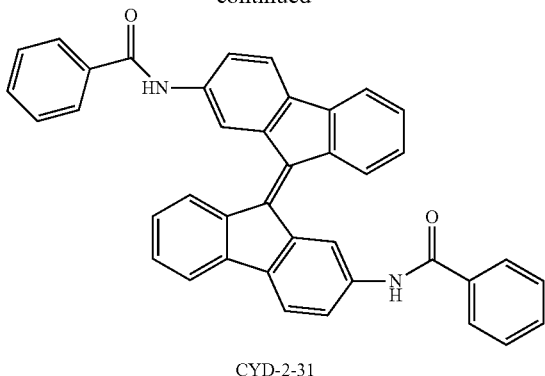

CYD-2-31

To a solution of cyclopropanesulfonic acid (9H-fluoren-2-yl)-amide (300 mg, 1.05 mmol) in 8 mL of THF was added salicylaldehyde (128 mg, 1.05 mmol), 40% NaOH (50 mg, 1.26 mmol) and Bu$_4$N$^+$Cl$^-$ (29 mg, 0.10 mmol), The resulting mixture was stirred at 65° C. for 48 hrs. After that, TLC showed that a new product was produce, and about half of the starting material was still remained. The reaction mixture was acidized with 10% HCl, and extracted with EtOAc for 3 times. The combined organic phase was concentrated under vacuum to give a yellow solid residue, which was purified by silica gel column; eluting with EtOAc/hexane=1:8 afforded 90 mg of CYD-2-31 as a yellow solid. $^1$H-NMR (600 MHz, d$_6$-DMSO) δ 10.48 (s, 2H), 8.12 (s, 2H), 7.98 (m, 6H), 7.76 (d, 2H J=7.8 Hz), 7.72 (d, 2H, J=7.2 Hz), 7.57 (m, 10H), 7.32 (m, 2H). $^{13}$C-NMR (150 MHz, CDCl$_3$) δ 166.1 (2C), 144.5 (2C), 140.8 (2C), 139.1 (2C), 135.8 (2C), 134.9 (2C), 134.3 (2C), 133.9 (2C), 132.2 (2C), 129.1 (2C), 128.8 (4C), 128.1 (4C), 126.2 (2C), 124.3 (2C), 121.9 (2C), 121.1 (2C), 116.2 (4C).

The dimmer of N-(9H-fluoren-2-yl)-3-nitro-benzenesulfonamide (CYD-2-38)

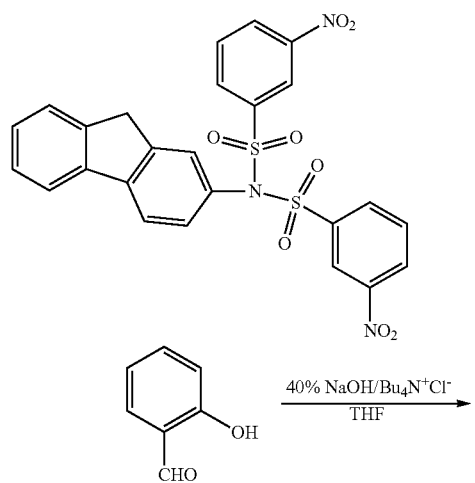

38
-continued

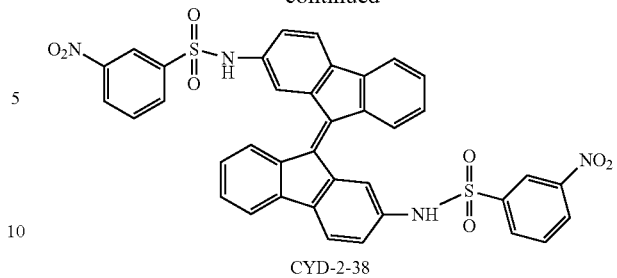

CYD-2-38

To a solution of N,N-di (3-nitro-benzenesulfonamide)-9H-fluoren-2-yl (800 mg, 1.45 mmol) in 20 mL of THF was added salicylaldehyde (212 mg, 1.74 mmol), 40% NaOH (75 mg, 1.89 mmol) and Bu$_4$N$^+$Cl$^-$ (40 mg, 0.14 mmol). The resulting mixture was stirred at 65° C. for 48 hrs. After that, TLC showed that a new product was produce, and about half of the starting material was still remained. The reaction mixture was acidized with 10% HCl, and extracted with EtOAc for 3 times. The combined organic phase was concentrated under vacuum to give a yellow solid residue, which was purified by silica gel column; eluting with CH$_2$Cl$_2$ afforded 130 mg of CYD-2-38 as a yellow solid. $^1$H-NMR (600 MHz, CDCl$_3$+CD$_3$OD) δ 8.67 (s, 2H), 8.37 (d, 2H, J=8.4 Hz), 8.13 (d, 2H, J=8.4 Hz), 7.68 (t, 2H, J=7.8 Hz), 7.57 (d, 2H, J=7.8 Hz), 7.41 (m, 10H), 7.25 (m, 1H). $^{13}$C-NMR (150 MHz, CDCl$_3$) δ 148.1 (2C), 143.8 (2C), 141.3 (2C), 141.1 (2C), 137.4 (2C), 135.1 (2C), 133.8 (2C), 132.5 (2C), 130.4 (2C), 128.8 (2C), 127.2 (2C), 127.0 (2C), 124.3 (2C), 122.1 (2C), 121.2 (4C), 120.2 (2C), 117.1 (4C).

The dimmer of cyclopropanesulfonic acid (9H-fluoren-2-yl)-amide (CYD-2-36)

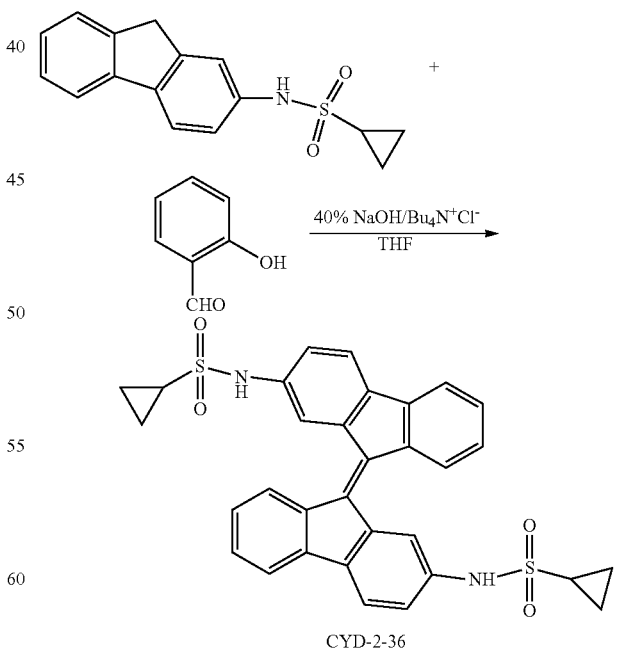

CYD-2-36

To a solution of cyclopropanesulfonic acid (9H-fluoren-2-yl)-amide (250 mg, 0.87 mmol) in 10 mL of THF was added salicylaldehyde (117 mg, 0.96 mmol), 40% NaOH (42 mg, 1.05 mmol) and Bu$_4$N$^+$Cl$^-$ (20 mg, 0.07 mmol). The resulting mixture was stirred at 65° C. for 48 hrs. After that, TLC showed that a new product was produce, and about half of the starting material was still remained. The reaction mixture was acidized with 10% HCl, and extracted with EtOAc for 3 times. The combined organic phase was concentrated under vacuum to give a yellow solid residue, which was purified by silica gel column; eluting with CH$_2$Cl$_2$ afforded 130 mg of CYD-2-36 as a yellow solid. $^1$H-NMR (600 MHz, CDCl$_3$+CD$_3$OD) δ 7.61 (d, 2H, J=6.6 Hz), 7.48 (m, 10H), 7.27 (m, 2H), 3.42 (br s, 1H), 2.53 (m, 2H), 1.18 (m, 4H), 0.99 (m, 4H). $^{13}$C-NMR (150 MHz, CDCl$_3$) δ 144.2 (2C), 140.6 (2C), 138.7 (2C), 135.2 (4C), 134.0 (2C), 128.7 (2C), 127.0 (2C), 124.4 (2C), 121.2 (2C), 120.2 (4C), 117.2 (2C), 29.9 (2C), 5.4 (4C).

1-(4-Chloro-benzyl)-3-(2-nitro-fluoren-9-ylidenemethyl)-1H-indole (CYD-2-21)

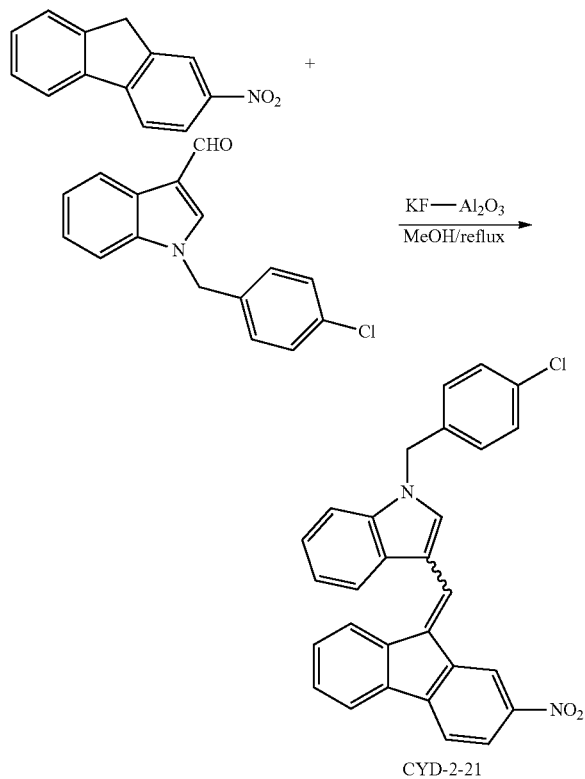

To a solution of 2-nitrofluorene (250 mg, 1.18 mmol) in 20 mL of methanol was added 1-(4-Chloro-benzyl)-1H-indole-3-carbaldehyde (382 mg, 1.42 mmol) and KF—Al$_2$O$_3$ (189 mg, 1.18 mmol). The resulting mixture was stirred at 85° C. for 18 hrs. After that, TLC showed that 2-nitrofluorene was gone, and many solids were suspended in MeOH. 260 mg of CYD-2-21 was obtained as a yellow solid after filtration and recrystallization from CH$_2$Cl$_2$. One isomer: $^1$H-NMR (600 MHz, d$_6$-DMSO) δ 8.96 (s, 1H), 8.41 (s, 1H), 8.27 (m, 2H), 8.18 (m, 3H), 8.09 (d, 1H, J=7.2 Hz), 7.78 (d, 1H, J=7.8 Hz), 7.62 (d, 1H, J=7.8 Hz), 7.47 (m, 5H), 7.28 (t, 1H, J=7.2 Hz), 7.20 (t, 1H, J=7.2 Hz), 5.57 (s, 2H). Another isomer: $^1$H-NMR (600 MHz, d$_6$-DMSO) δ 9.01 (s, 1H), 8.39 (s, 1H), 8.33 (s, 1H), 8.19 (m, 4H), 7.86 (d, 1H, J=8.4 Hz), 7.78 (d, 1H, J=7.8 Hz), 7.62 (d, 1H, J=7.8 Hz), 7.47 (m, 5H), 7.28 (t, 1H, J=7.2 Hz), 7.20 (t, 1H, J=7.2 Hz), 5.59 (s, 2H). $^{13}$C-NMR (150 MHz, d$_6$-DMSO) δ 147.1, 146.6, 145.6, 142.9, 141.9, 141.0, 138.2, 138.0, 137.0, 136.8, 136.7, 136.4 (2C), 135.6, 132.7, 132.2, 132.1, 130.2, 129.9, 129.8, 129.7, 129.2, 129.1, 129.0 (2C), 128.4, 128.1 (2C), 127.9, 124.5, 124.1, 123.8, 123.2 (2C), 123.1, 122.4, 122.0, 121.7, 121.2, 121.0 (2C), 120.8, 120.6 (2C), 120.2, 118.8, 118.7, 116.2 (2C), 111.5, 111.4, 111.3 (2C), 49.4, 49.2.

2-[3-(2-Nitro-fluoren-9-ylidenemethyl)-pyridin-2-yloxy]-ethylamine (CYD-4-61)

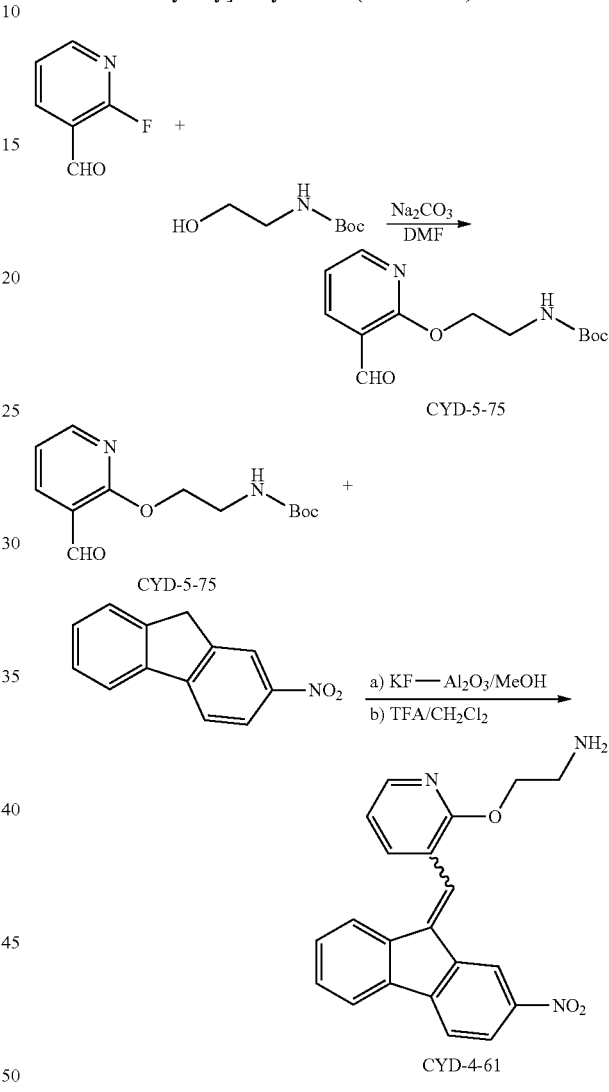

To a solution of 2-fluoro-pyridine-3-carbaldehyde (500 mg, 3.995 mmol) and (2-hydroxy-ethyl)-carbamic acid tert-butyl ester (1287 mg, 7.99 mmol) in 20 mL of DMF was added Na$_2$CO$_3$ (847 mg, 7.99 mmol). The resulting mixture was stirred at 80° C. for 5 hrs and the reaction progress was monitored by TLC analysis. The reaction mixture was then washed with brine, and concentrated under vacuum to give an oil residue, which was purified by silica gel column; eluting with EtOAc/hexane=1:2 to afford 600 mg of CYD-5-75 in 60% yield as colorless gel. To a solution of 2-nitrofluorene (244 mg, 1.15 mmol) and CYD-5-75 (220 mg, 0.82 mmol) in 20 mL of methanol was added KF—Al$_2$O$_3$ (184 mg, 1.15 mmol). The resulting mixture was stirred at 72° C. After 6 hrs, TLC indicated that the starting material was gone. 40 mL of CH$_2$Cl$_2$ was added into the reaction mixture. The insoluble solid was filtrated, and the filtrate was concentrated under vacuum to give a yellow solid, which was recrystallized from alcohol and CH$_2$Cl$_2$ to give 120 mg of a yellow solid. The yellow solid (180 mg, 0.39 mmol) was dissolved in 4 mL of CH$_2$Cl$_2$, and then 1 mL of TFA was added into it at 0° C. The resulting mixture was stirred at rt for 4 hrs. The reaction mixture was washed with sat. NaHCO$_3$ (aq.), and concentrated under vacuum to give an oil residue, which was purified by silica gel column; eluting with CH$_2$Cl$_2$/MeOH=20:1 to provide 150 mg of CYD-4-61 as yellow solid in 50% yield for two steps. $^1$H-NMR (600 MHz, CDCl$_3$) δ 8.61 (d, 1H, J=1.8 Hz), 8.40 (d, 1H, J=2.4 Hz), 8.27 (m, 2H), 8.23 (dd, 1H, J=2.4 Hz, 8.4 Hz), 8.18 (dd, 1H, J=1.8 Hz, 7.8 Hz), 7.89 (m, 3H), 7.76 (m, 4H), 7.72 (s, 1H), 7.68 (s, 1H), 7.61 (d, 1H, J=7.8 Hz), 7.45 (m, 2H), 7.39 (m, 1H), 7.23 (m, 1H), 7.04 (m, 1H), 7.00 (m, 1H), 4.46 (m, 4H), 3.07 (m, 4H), 1.45 (br s, 4H). $^{13}$C-NMR (150 MHz, CDCl$_3$) δ 161.3, 161.2, 148.0, 147.7, 147.1, 146.6 (2C), 144.4, 140.7, 139.9, 139.5, 139.4, 138.9, 137.8, 136.8, 136.6, 135.5, 135.4, 129.2, 129.0, 128.9, 128.7, 124.6, 124.5, 124.3, 124.0, 123.7, 121.2, 120.9, 119.7, 119.6, 119.4, 118.7, 118.4, 116.7, 116.6, 116.1, 68.8, 68.7, 41.3 (2C). HRMS calc. for C$_{21}$H$_{17}$N$_3$O$_3$ [M+H]$^+$ 360.1343; found 360.1351. HPLC purity 99.2%

Figure 5A:
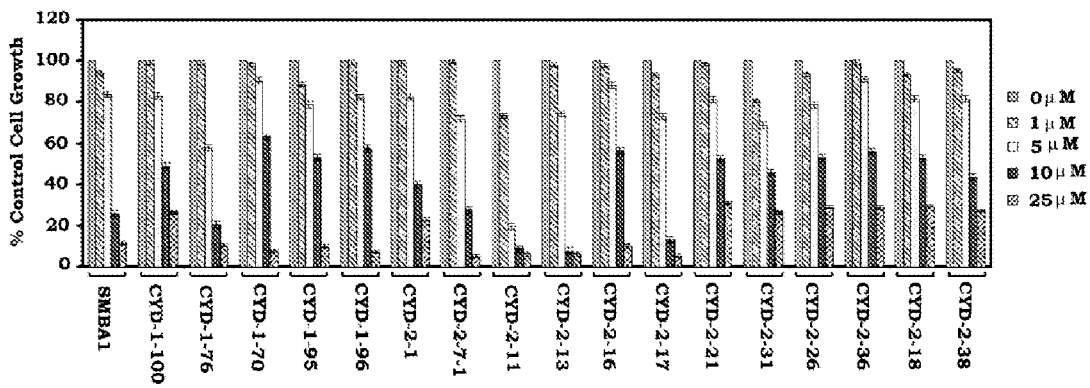
FIGS. 5A-C show data from the sulforhodamine B (SRB) assay for suppressing lung cancer growth.
Figure 5B:
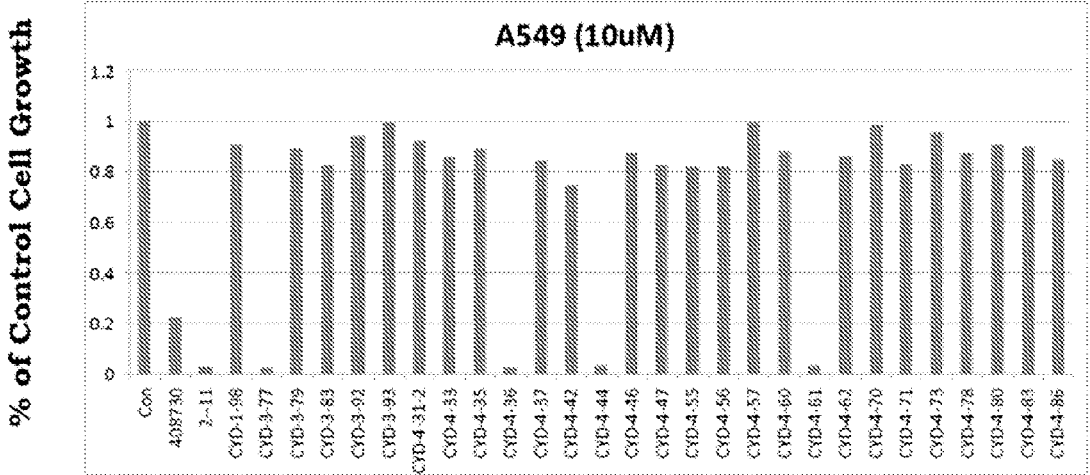

Using appropriate starting materials and the same or appropriately modified protocols, the follow compounds were prepared and tested (See FIG. 5B, C). In certain embodiments the compounds are selected from.

CYD-1-98

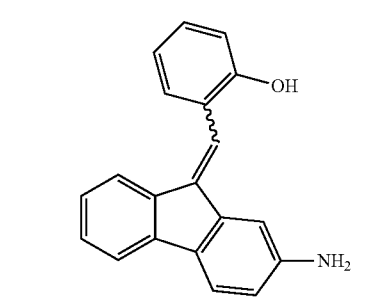

CYD-3-77

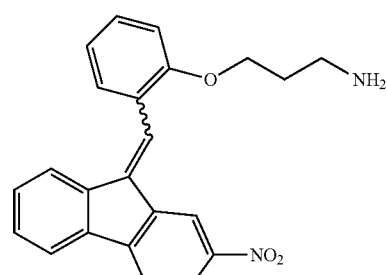

CYD-3-79

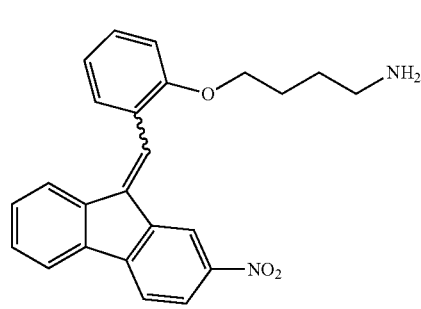

CYD-3-83

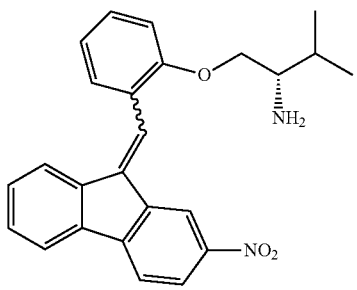

CYD-3-92

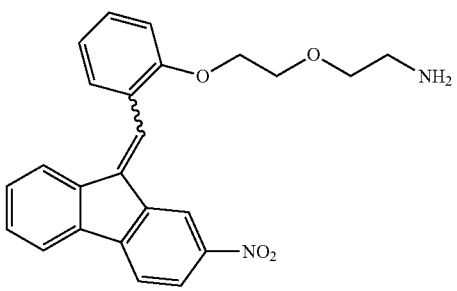

CYD-3-93

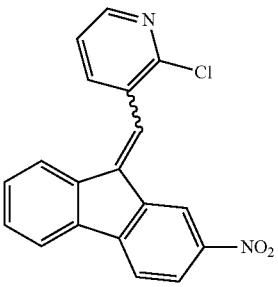

CYD-4-31-2

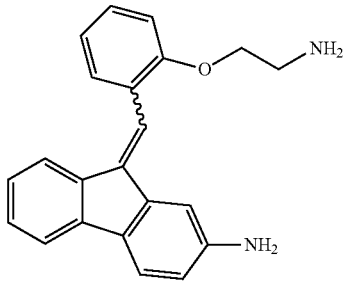

CYD-4-33

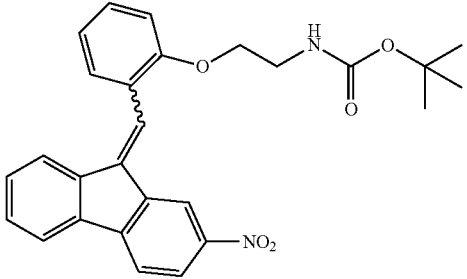

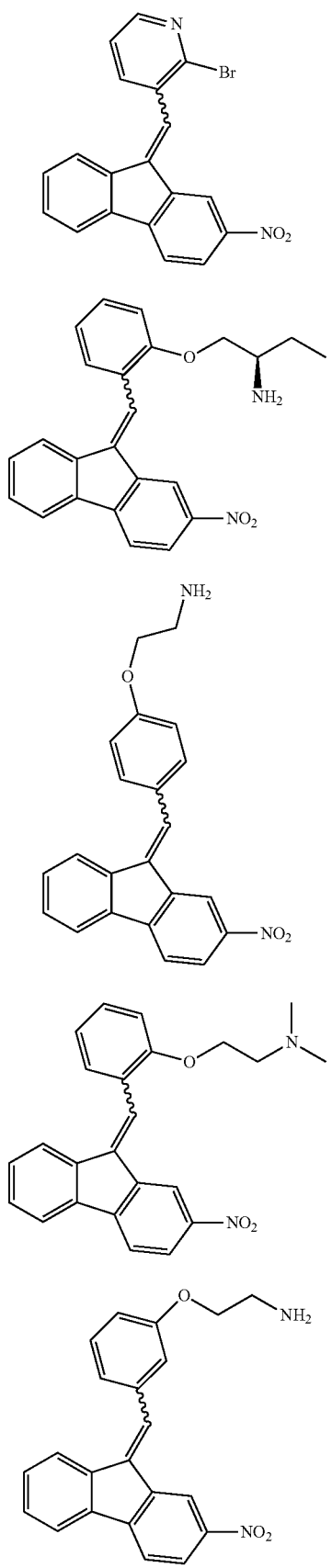
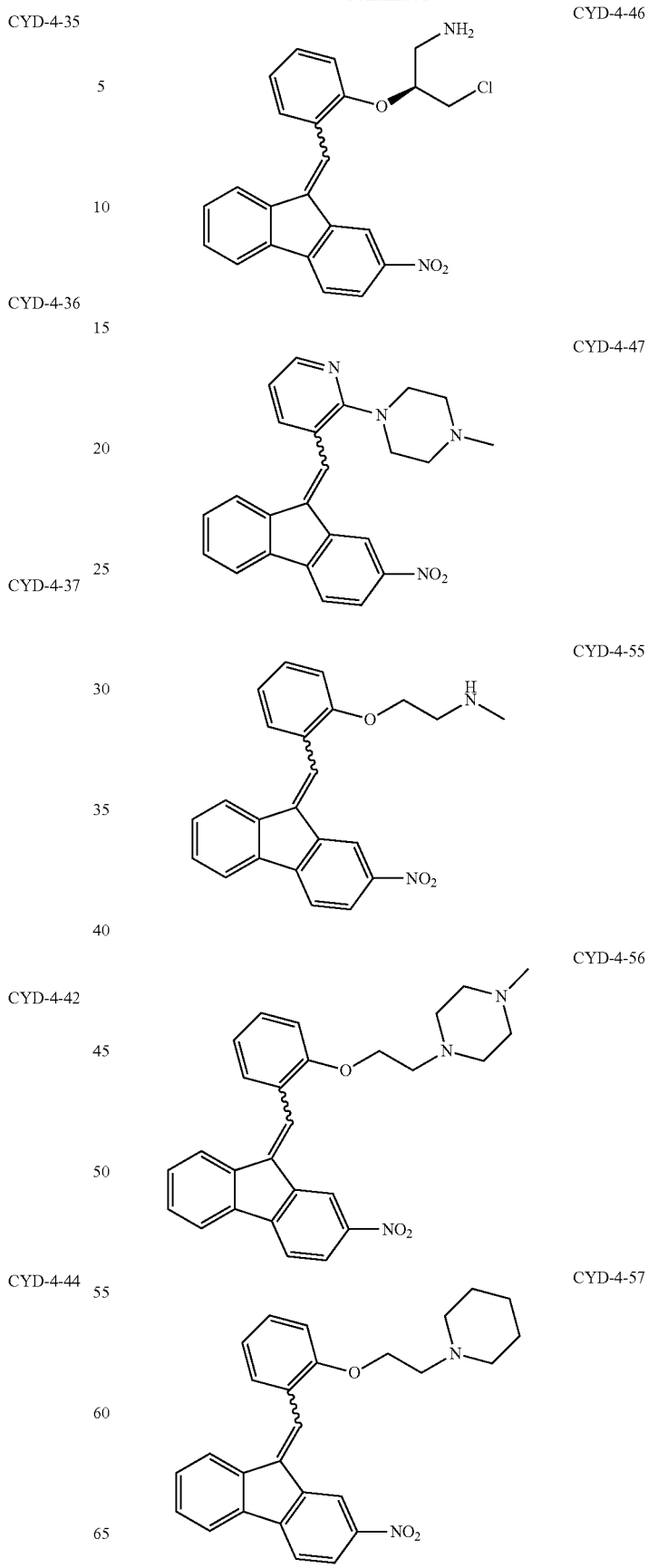

CYD-4-60
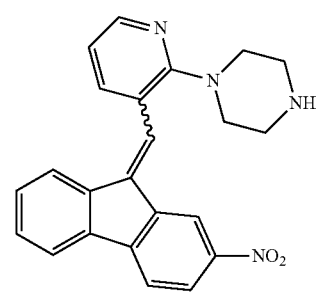
CYD-4-61
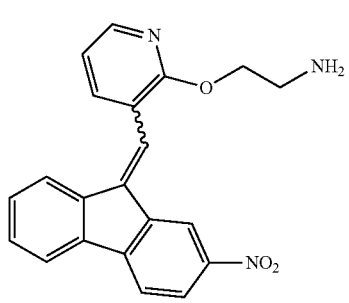
CYD-4-62
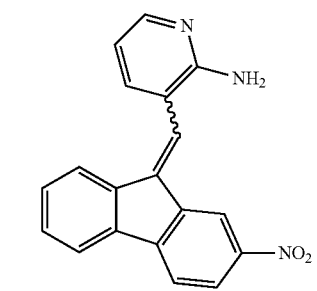
CYD-4-70
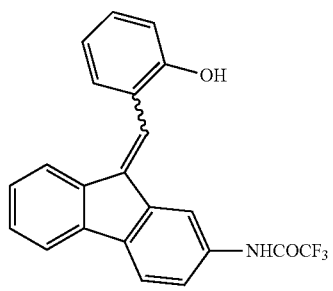
CYD-4-71
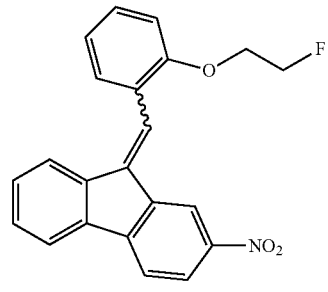
CYD-4-73
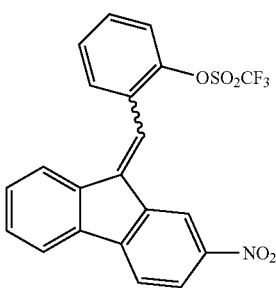
CYD-4-78
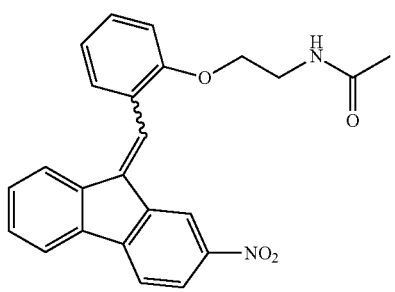
CYD-4-80
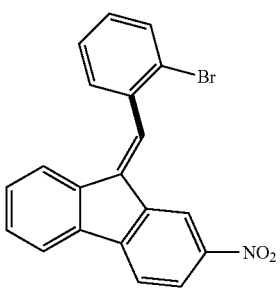
CYD-4-83
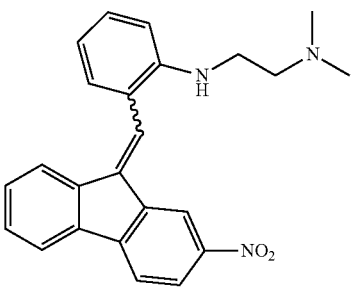
CYD-4-86
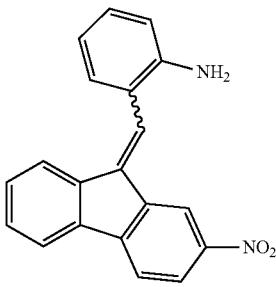
or salts thereof.

Assays

Suppressing Lung Cancer Growth

Figure 5C:
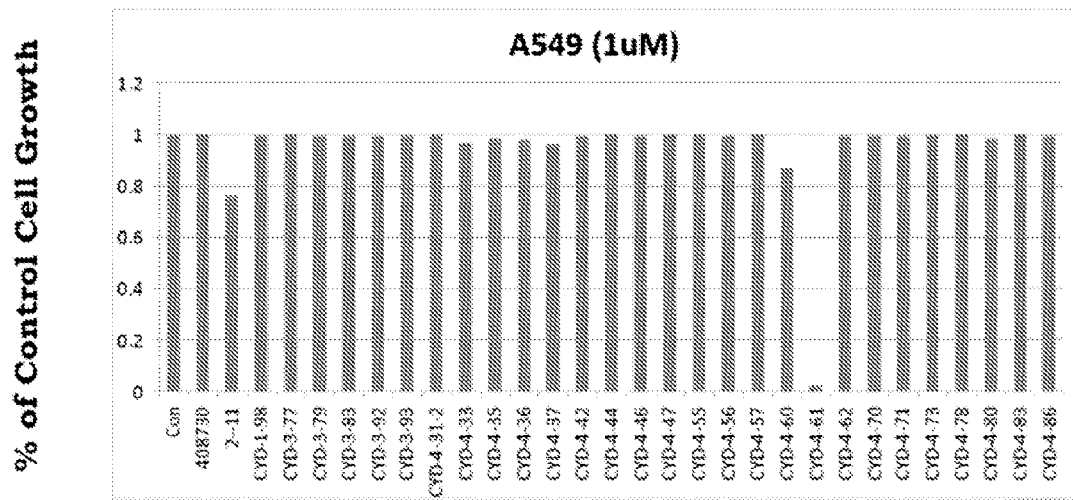
Figure 6:
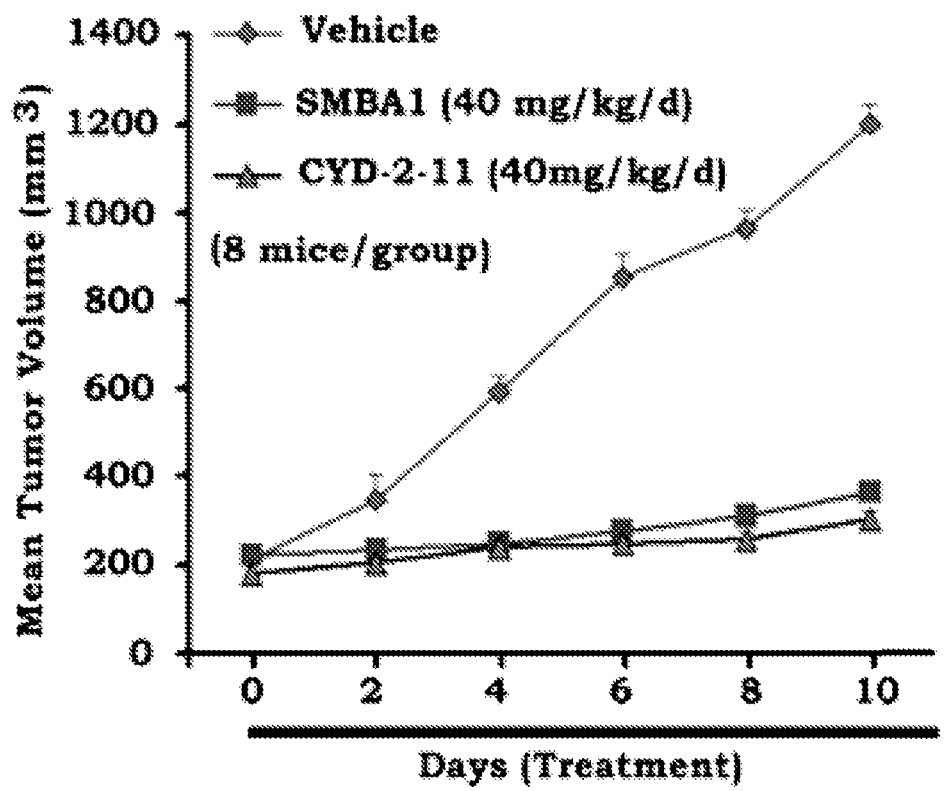
FIG. 6 shows in vivo anti-lung cancer activity of SMBA1 and its analog (CYD-2-11).
Figure 6:
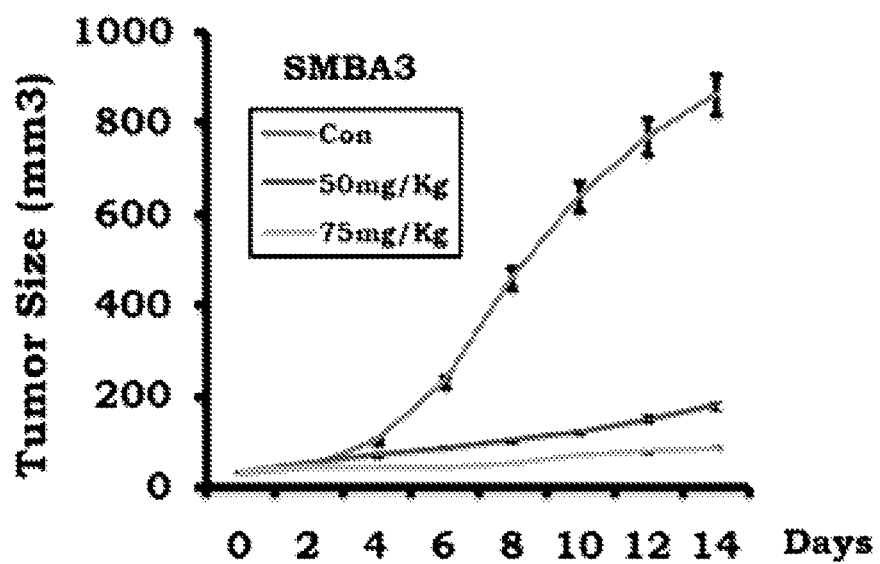

To compare sensitivities of the compounds, A549 human lung cancer cells were treated with increasing concentrations (0, 1, 5, 10, 25 µM) of 2-(2-Nitro-fluoren-9-ylidenemethyl)-phenol (CYD-1-87) and derivatives for 48 h. The surviving cell fraction was determined using the sulforhodamine B (SRB) assay as described in (Vichai & Kirtikara, Nat Protoc 1, 1112-1116, 2006 hereby incorporated by reference). The sulforhodamine B (SRB) assay is used for cell density determination, based on the measurement of cellular protein content. The method described here has been optimized for the toxicity screening of compounds to adherent cells in a 96-well format. After an incubation period, cell monolayers are fixed with 10% (wt/vol) trichloroacetic acid and stained for 30 min, after which the excess dye is removed by washing repeatedly with 1% (vol/vol) acetic acid. The protein-bound dye is dissolved in 10 mM Tris base solution for OD determination at 510 nm using a microplate reader. The results are typically linear over a 20-fold range of cell numbers. CYD-2-11 has an $IC_{50}$ of 1.93 µM, Derivative CYD-2-17 has an $IC_{50}$ of 5.08 µM and CYD-2-13 has an $IC_{50}$ of 5.91 µM. Data additional obtained from this assay is provided in FIG. 5. SMBA1 has an $IC_{50}$ of 7.35 and CYD-4-61, 2-((3-((2-nitro-fluoren-9-ylidene)methyl)pyridin-2-yl)oxy)ethanamine has an $IC_{50}$ of 0.026.

The invention claimed is:

1. A compound of Formula IB,

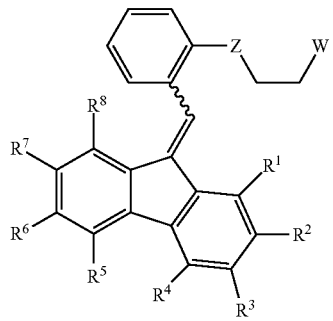

Formula IB or salt thereof wherein,

Z is O, S, $CH_2$, or NH;

W is hydroxy, amino, alkylamino, dialkylamino, aryl, or heterocyclyl wherein W is optionally substituted with one or more $R^{11}$;

$R^1$, $R^3$, $R^4$, $R^5$, $R^6$, $R^7$, and $R^8$ are each individually and independently hydrogen, alkyl, halogen, nitro, cyano, hydroxy, amino, mercapto, formyl, carboxy, carbamoyl,

SEQUENCE LISTING

<160> NUMBER OF SEQ ID NOS: 1

<210> SEQ ID NO 1
<211> LENGTH: 192
<212> TYPE: PRT
<213> ORGANISM: Homo sapiens

<400> SEQUENCE: 1

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190 alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, $R^4$, $R^5$, $R^6$, $R^7$, and $R^8$ are optionally substituted with one or more, the same or different $R^{10}$;

$R^2$ is nitro or amino wherein $R^2$ is optionally substituted with one or more, the same or different $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound claim 1, wherein $R^2$ is nitro.

3. The compound of claim 1, selected from the group:
4-{2-[2-(2-Nitro-fluoren-9-ylidenemethyl)-phenoxy]-ethyl}-morpholine;
1-{2-[2-(2-Nitro-fluoren-9-ylidenemethyl)-phenoxy]-ethyl}-piperazine;
2-[2-(2-Nitro-fluoren-9-ylidenemethyl)-phenoxy]-ethanol;
2-[2-(2-Nitro-fluoren-9-ylidenemethyl)-phenoxy]-ethylamine;
4-[2-(2-Nitro-fluoren-9-ylidenemethyl)-phenoxy]-piperidine;
1-(4-Fluoro-benzenesulfonyl)-4-{2-[2-(2-nitro-fluoren-9-ylidenemethyl)-phenoxy]-ethyl}-piperazine;
1-(4-{2-[2-(2-Nitro-fluoren-9-ylidenemethyl)-phenoxy]-ethyl}-piperazin-1-yl)-ethanone;
1-Cyclopropanesulfonyl-4-{2-[2-(2-nitro-fluoren-9-ylidenemethyl)-phenoxy]-ethyl}-piperazine; and
1-Methanesulfonyl-4-{2-[2-(2-nitro-fluoren-9-ylidenemethyl)-phenoxy]-ethyl}-piperazine
or salts thereof.

4. A pharmaceutical composition comprising a compound of claim 1, and a pharmaceutically acceptable excipient.

5. The pharmaceutical composition of claim 4, further comprising a second therapeutic agent.

6. A method of treating breast cancer comprising administering a pharmaceutical composition of claim 4 to a subject diagnosed with, exhibiting symptoms of, or at risk of cancer.

7. The method of claim 6, wherein the pharmaceutical compositions is administered in combination with a second chemotherapeutic agent.

8. The method of claim 7, wherein the second chemotherapeutic agent is gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib, anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

* * * * *